(12) United States Patent (10) Patent No.: US 9,114,117 B2
Schmidt-Wolf (45) Date of Patent: Aug. 25, 2015

(54) COMPOUNDS EFFECTIVE AGAINST CANCER

(75) Inventor: Ingo Schmidt-Wolf, Bonn (DE)

(73) Assignee: Ingo Schmidt-Wolf, Bonn (DE)

( * ) Notice: Subject to any disclaimer, the term of this patent is extended or adjusted under 35 U.S.C. 154(b) by 603 days.

(21) Appl. No.: 13/144,392

(22) PCT Filed: Jan. 13, 2009

(86) PCT No.: PCT/EP2009/000150
§ 371 (c)(1),
(2), (4) Date: Oct. 5, 2011

(87) PCT Pub. No.: WO2010/081486
PCT Pub. Date: Jul. 22, 2010

(65) Prior Publication Data
US 2012/0028993 A1 Feb. 2, 2012

(51) Int. Cl.
*A61K 31/19* (2006.01)
*A61K 31/192* (2006.01)
*A61K 31/4418* (2006.01)

(52) U.S. Cl.
CPC ........... *A61K 31/192* (2013.01); *A61K 31/4418* (2013.01); *A61K 31/19* (2013.01)

(58) Field of Classification Search
CPC ..................................................... A61K 31/19
USPC ......................................................... 514/570
See application file for complete search history.

(56) References Cited

U.S. PATENT DOCUMENTS

2008/0207738 A1* 8/2008 Kiss .............................. 514/437

FOREIGN PATENT DOCUMENTS

KR 20020026743 A 4/2002

OTHER PUBLICATIONS

Office Action issued for European Patent Application No. 09776313, dated Oct. 23, 2013, 2 pages.
Wilson Y et al: "Ethacrynic acid modulates the in vitro cytotoxicity of mitoxantrone in MCF 7 human breast cancer cells" British Journal of Clinical Pharmacology, Blackwell Scientific Publ, GB, vol. 40, No. 2, Aug. 1, 1995, p. 190P, XP009123135 ISSN: 0306-5251 abstract.
Rhodes T et al: "A Study of Ethacrynic Acid as a Potential Modifier of Melphalan and Cisplatin Sensitivity in Human Lung Cancer Parental and Drug-Resistant Cell Lines" British Journal of Cancer,
Nature Publishing Group, London, GB, vol. 65, No. 5, Jan. 1, 1992, pp. 684-690, XP009123131 ISSN: 0007-0920 abstract.
Nemec J N et al: "The use of thyroid-stimulating hormone-Edecrine pretreatment in the radioiodide therapy of metastatic thyroid cancer. Clinical tolerance and changes in the radioiodine kinetics" Neoplasma, Sciences, vol. 19, No. 2, Jan. 1, 1972, pp. 125-133, XP009123128 ISSN: 0028-2685 abstract.
Lacreta Frank P et al: "Pharmacokinetics and bioavailability study of ethacrynic acid as a modulator of drug resistance in patients with cancer" Journal of Pharmacology and Experimental Therapeutics, American Society for Pharmacology and Experimental Therapeutics, US, vol. 270, No. 3, Sep. 1, 1994, pp. 1186-1191, XP009123137 ISSN: 0022-3565 abstract.
International Search Report from International Application No. PCT/EP2009/00150, (2009).
Official Communication issued on Nov. 30, 2012 in counterpart European Patent Application No. 09776313.0-2123.

* cited by examiner

*Primary Examiner* — Raymond Henley, III
(74) *Attorney, Agent, or Firm* — Morgan, Lewis & Bockius, LLP

(57) ABSTRACT

The present invention describes a Composition, comprising one or more compounds selected from the group consisting of a) compound (I) which is ethacrynic acid bezafibrate, fenofibrate, and/or griseofulvin, b) compound (II), which is ciclopirox ciclopirox olamine, octopirox, and/or cinnarizine, c) mixtures of compound (I) and compound (II), or pharmaceutically acceptable derivatives thereof for the treatment of cancer. The present invention is further directed to the use of said compounds or a mixture of compounds for the manufacture of a medicament for the treatment of cancer and to the use of said compound in a method for treating cancers in animals and humans.

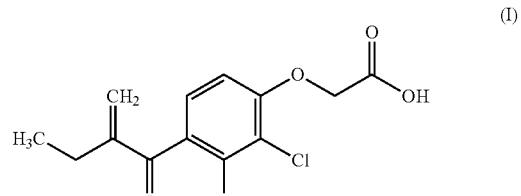

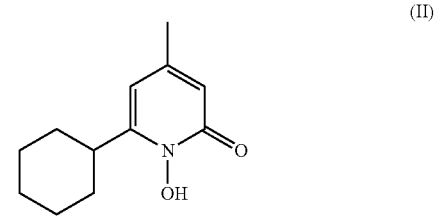

2 Claims, 14 Drawing Sheets

72 h                                Culture-control

PBMCs

LAM-53

DHL-4

OPM-2

Raji

72 h  (A) DMSO-control   (B) EA (30 μM) + cic (10 μM)

PBMCs

LAM-53

DHL-4

OPM-2

Raji

72 h (A) EA (30 μM)  (B) cic (10 μM)

PBMCs

LAM-53

DHL-4

OPM-2

Raji

COMPOUNDS EFFECTIVE AGAINST CANCER

CROSS-REFERENCE TO RELATED APPLICATIONS

This application claims priority to International Patent Application No. PCT/EP2009/000150 filed 13 Jan. 2009, the contents of which are hereby incorporated by reference in their entireties.

DETAILED DESCRIPTION

The present invention is directed a composition comprising a compound selected from the group consisting of a) compound (I) which is ethacrynic acid, bezafibrate, fenofibrate, and/or griseofulvin, b) compound (II), which is ciclopirox, ciclopirox olamine, octopirox, and/or cinnarizine, c) mixtures of compound (I) and compound (II), or pharmaceutically acceptable derivatives thereof for the treatment of cancer. The present invention is further directed to the use of said compounds or a mixture of compounds for the manufacture of a medicament for the treatment of cancer and to the use of said compound in a method for treating cancers in animals and humans.

Ethacrynic acid is a compound of the structural formula

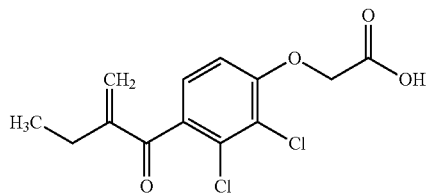 [SMILES: C=C(CC)C(=O)c1ccc(OCC(=O)O)c(Cl)c1Cl]

The systematic (IUPAC) name for ethacrynic acid is 2-[2,3-dichloro-4-(2-methylidenebutanoyl)phenoxy]acetic acid.

Ethacrynic acid (EA) is known as a potent diuretic. Therefore, diuresis with water and electrolyte depletion is the consequence, if excessive amounts are administered. EA is an unsaturated ketone derivative of an aryloxyacetic acid and chemically designated as [2,3-dichloro-4-(2-methylene-1-oxobutyl)phenoxy]acetic acid. It is a white, crystalline powder which is slightly soluble in water, but soluble in most organic solvents e.g. alcohols, chloroform, and benzene. The sodium salt of EA is Ethacrynate sodium and also available as diuretic agent (Tablets Edecrin (Ethacrynic acid) and intravenous Sodium Edecrin (Ethacrynate sodium) (2005). Merck & Co., Inc. Whitehouse Station, N.Y., USA). In human tumors as well as in many animal models of carcinogenesis, glutathione-S-transferase P (GST-P) is overexpressed (Mccaughan et al, 1994). There are seven classes of glutathione-S-transferases (GSTs) in a family of dimeric enzymes performing multiple functions. One of them is the conjugation of glutathione (GSH) with electrophilic compounds (Aizawa et al, 2003). GSH is a tripeptide of the amino acids glutamine (Glu), cysteine (Cys) and glycine (Gly) forming the compound γ-glutamyl-cysteinyl-glycine. It acts as a reducing agent and as an antioxidant. The conjugation of GSH with toxic compounds forms mercapturates catalyzed by the GSTs. This process forms S-substituted Cys by the release of Glu and Gly residues. Finally, a mercapturic acid which can be excreted in urine is formed by the acetylation of the cysteinyl amino group (Estrela et al, 2006). The pi-class GSTs, as GST-P in rats and GST P1-1 in humans appear in an association with neoplastic development and anticancer drug resistance. EA is a GST P1-1 inhibitor with the induction of apoptosis in some cell lines (Aizawa et al, 2003). It has been shown to bind GSTs. The in vitro cytotoxicity of chemotherapeutic agents tested in cell lines could be enhanced by EA (Nagourney et al, 1990).

Ciclopirox is a compound of the structural formula

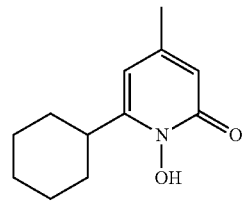

The systematic (IUPAC) name of ciclopirox is 6-cyclohexyl-1-hydroxy-4-methyl-1,2-dihydropyridin-2-one. Ciclopirox is often used as ciclopirox olamine.

Ciclopirox olamine (cic) is a synthetic antifungal agent which is used topical for the treatment of yeast infections in humans (Penlac (ciclopirox) Topical Solution, 8% (2005), Dermik Laboratories, Berwyn, Pa., USA; Hoffman et al, 1991). Ciclopirox is a hydroxypyridone derivative and the free acid of cic. Nevertheless, there is an identical spectrum of activity between cic and ciclopirox (Nail Batrafen, Ciclopirox 8% Nail Lacquer (1999), Hoechst Marion Roussel (NZ) Limited, Penrose, Auckland). Ciclopirox is chemically designed as 6-Cyclohexyl-1-hydroxy-4-methyl-2(1H)-pyridone (Szüts et al, 2004). It is a white powder, soluble in methanol. The main metabolic pathway how cic is degraded is glucuronidation based on the secretion of glucuronides (Penlac (ciclopirox) Topical Solution, 8% (2005), Dermik Laboratories, Berwyn, Pa., USA). Cic, as a chelator of polyvalent metal cations (e.g. $Fe^{3+}$ and $Al^{3+}$), inhibits the metal-dependent enzymes occurring in the metabolism of a cell (Penlac (ciclopirox) Topical Solution, 8% (2005), Dermik Laboratories, Berwyn, Pa., USA; Nail Batrafen, 1999). It blocks reversibly the cell cycle near the G1/S phase boundary, tested on HL-60 pro-myeloid leukemia cells (Hoffman et al, 1991).

BRIEF DESCRIPTION OF THE DRAWINGS

In FIG. 5 (A) samples were measured after 24, 48 and 72 h. After 0 h, the time of execution, the relative viability was defined as 100% for all samples. In FIG. 5 (B) the relative viability values for the samples measured after 24, 48 and 72 h.

In FIG. 6 (A) samples were measured after 24, 48 and 72 h. After 0 h, the time of execution, the relative apoptosis was defined as 0% for all samples. In FIG. 6 (B) the relative apoptosis values for the samples measured after 24, 48 and 72 h.

In FIG. 7 (A) samples were measured after 24, 48 and 72 h. After 0 h, the time of execution, the relative viability was defined as 100% for all samples. In FIG. 7 (B) the relative viability values for the samples measured after 24, 48 and 72 h.

In FIG. 8 (A) samples were measured after 24, 48 and 72 h. After 0 h, the time of execution, the relative apoptosis was defined as 0% for all samples. In FIG. 8 (B) the relative apoptosis values for the samples measured after 24, 48 and 72 h.

In FIG. 9 (A) samples were measured after 24, 48 and 72 h. After 0 h, the time of execution, the relative viability was defined as 100% for all samples. In FIG. 9 (B) the relative viability values for the samples measured after 24, 48 and 72 h.

In FIG. 10 (A) samples were measured after 24, 48 and 72 h. After 0 h, the time of execution, the relative apoptosis was defined as 0% for all samples. In FIG. 10 (B) the relative apoptosis values for the samples measured after 24, 48 and 72 h.

In FIG. 11 (A) samples were measured after 24, 48 and 72 h. After 0 h, the time of execution, the relative viability was defined as 100% for all samples. In FIG. 11 (B) the relative viability values for the samples measured after 24, 48 and 72 h.

In FIG. 12 (A) samples were measured after 24, 48 and 72 h. After 0 h, the time of execution, the relative apoptosis was defined as 0% for all samples. In FIG. 12 (B) the relative apoptosis values for the samples measured after 24, 48 and 72 h.

In FIG. 13 (A) samples were measured after 24, 48 and 72 h. After 0 h, the time of execution, the relative viability was defined as 100% for all samples. In FIG. 13 (B) the relative viability values for the samples measured after 24, 48 and 72 h.

In FIG. 14 (A) samples were measured after 24, 48 and 72 h. After 0 h, the time of execution, the relative apoptosis was defined as 0% for all samples. In FIG. 14 (B) the relative apoptosis values for the samples measured after 24, 48 and 72 h.

Figure 1:
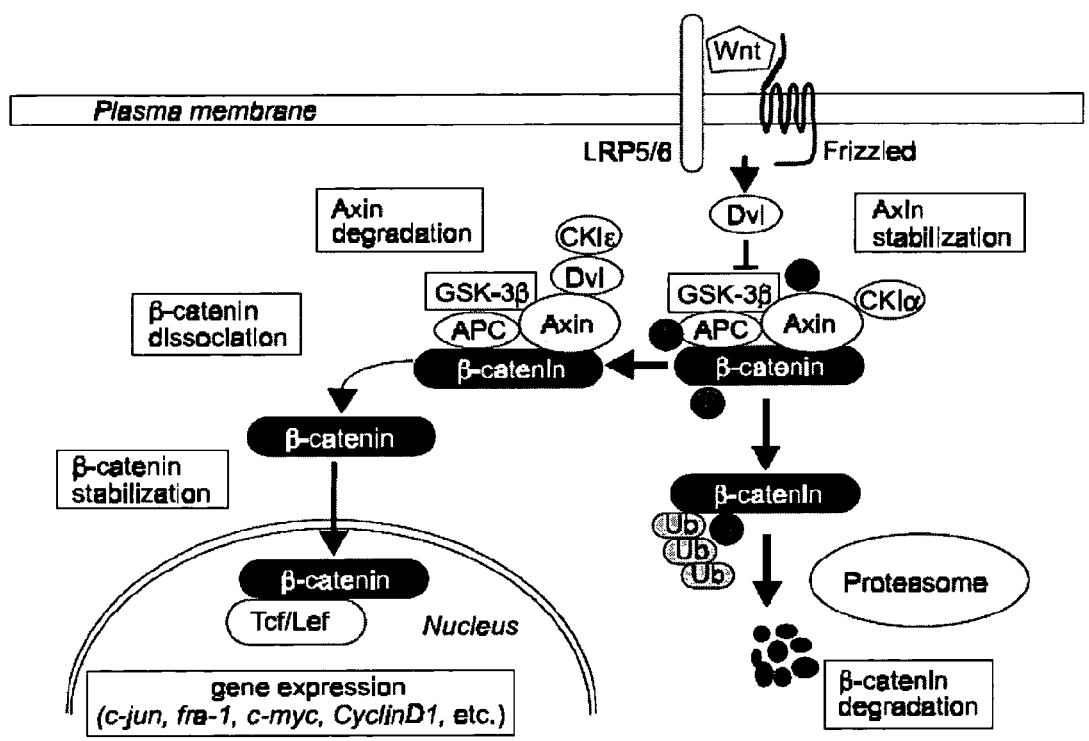
FIG. 1 is a graph illustrating molecular signaling pathways.

There are 19 known Wingless-Int (Wnt) genes found in the human and mouse genome, which comprise a family of secreted glycoproteins involved in cell proliferation, differentiation, and oncogenesis. The Wnts induce a signaling cascade and regulate early B cell growth and survival by stabilization of β-catenin (Lu et al, 2004; Kikuchi et al, 2006). Therefore an aberrant activation of the Wnt signaling cascade leads to oncogenesis. In comparison with normal B and T cells, there is an overexpression of the Wnt3 gene detected in B cell chronic lymphocytic leukemia (CLL) (Lu et al, 2004). The receptor complex of the ligand (Wnt) consists of a receptor of the Frizzled (Fzd) family and of the low-density lipoprotein-receptor-related proteins (LRP) 5 and 6. When Wnt binds to its receptor complex, β-catenin is stabilized by the phosphoprotein Dishevelled (Dvl) which inhibitits the phosphorylating effect of glycogen synthase kinase (GSK)-3β in the Axin complex. The phosphorylated form of β-catenin would be ubiquitinated and degraded by the proteasome (Kikuchi et al, 2006). Unphosphorylated β-catenin in the cytoplasm leads to a translocation into the nucleus (Lu et al, 2004). Thus, accumulation of unphosphorylated β-catenin in the nucleus activates transcription factors of the T cell (TCF) and lymphoid-enhancing (LEF) family and stimulates the expression of genes such as c-myc, c-jun, fra-1, and cyclin D1 (Kikuchi et al, 2006). This is the mechanism of the classical or canonical Wnt signaling cascade. The activation of the Wnt/β-catenin pathway can be inhibited by R-etodolac, the R-enantiomer of a nonsteroidal antiinflammatory drug (Lu et al, 2004) (see FIG. 1).

In the β-Catenin pathway, cytoplasmic β-catenin is destabilized by a multi-protein complex containing GSK-3β, CKIα and APC in the absence of Wnt. β-Catenin is phosphorylated by CKIα and GSK-3β efficiently in this complex, and phosphorylated β-catenin is ubiquitinated and degraded by the proteasome. When Wnt binds to its cell surface receptor consisting of Frizzled and LRP5/6, the phosphorylation of β-catenin by GSK-3β is suppressed, and consequently β-catenin is accumulated in the cytosol. The accumulated β-catenin is translocated in the nucleus, where it binds to and activates Tcf/Lef, resulting in expression of the target genes (Kikuchi et al, 2006) (see FIG. 1).

Besides interrupting the Wnt/β-catenin cascade, the drug EA is tested to target the GST and deplete GSH while dc is used to intent an interruption in the cell cycle at the restriction point. An extended variety of anticancer drugs with different targets can enclose more opportunities in the prevention and proceeding against the development of cancer.

It was the object underlying the present invention to provide compounds for the treatment of cancer. It was the further object of the present invention to provide the use of such compounds for the manufactures of a medicament for the treatment of cancer. It was a yet further object of the present invention to provide a method for treating cancer in animals and humans by administering such compounds.

Said object is solved by a composition, comprising one or more compounds selected from the group consisting of
a) compound (I) which is
    ethacrynic acid

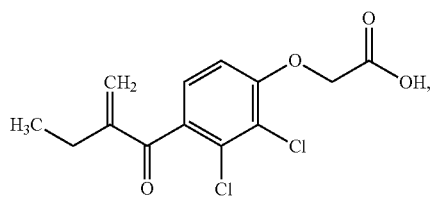 [SMILES: C=C(CC)C(=O)c1ccc(OCC(=O)O)c(Cl)c1Cl]

bezafibrate, fenofibrate, and/or griseofulvin,
b) compound (II), which is
    ciclopirox

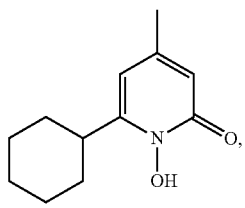

ciclopirox olamine, octopirox, and/or cinnarizine,
c) mixtures of compound (I) and compound (II),
or pharmaceutically acceptable derivatives thereof for the treatment of cancer.

In particular, the object underlying the present invention is solved by a compound selected from the group consisting of
a) compound (I) which is
    ethacrynic acid

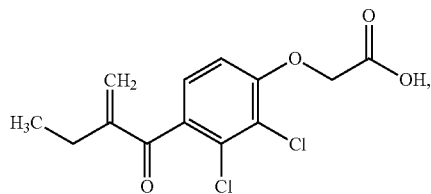 [SMILES: C=C(CC)C(=O)c1ccc(OCC(=O)O)c(Cl)c1Cl]

bezafibrate, fenofibrate, and/or griseofulvin,
b) compound (II), which is
    ciclopirox

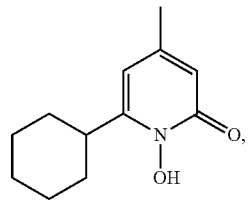

ciclopirox olamine, octopirox, and/or cinnarizine,
c) mixtures of compound (I) and compound (II),
or pharmaceutically acceptable derivatives thereof for the treatment of myeloma, lymphoma and leukemia.

Bezafibrate is a fibrate drug previously used for the treatment of hyperlipidaemia and which has the systematic (IUPAC) name 2-(4-{2-[4-chlorophenyl)formamido]ethyl}phenoxy)-2-methylpropanoic acid.

Fenofibrate is a drug of the fibrate class which has previously been used to reduce cholesterol levels and which has the systematic (IUPAC) name propan-2-yl 2-{4-[(4-chlorophenyl)carbonyl]phenoxy}-2-methylpropanoate.

Griseofulvin is a compound which has previously been used as an antifungal drug and which has the systematic (IUPAC) name (2S,6'R)-7-chloro-2',4,6-trimethoxy-6'methyl-3H-spiro[1-benzofuran-2,1'-cyclohexan]-2'-ene-3,4'-dione.

Octopirox, also known as piroctone olamine, is a compound previously used in the treatment of fungal infections and has the structural formula

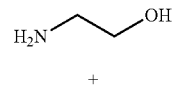

+

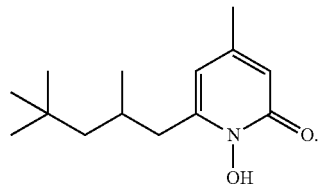

Cinnarizine is a compound which has previously been used as an antihistaminic drug and which has the systematic (IUPAC) name 1-benzhydryl-4-cinnamyl-piperazine.

In a preferred embodiment, the composition described above is adapted for oral, parenteral, rectal, nasal, vaginal, or topical administration.

The invention is also directed to the use of a composition comprising one or more compounds selected from the group consisting of
a) compound (I) which is
    ethacrynic acid

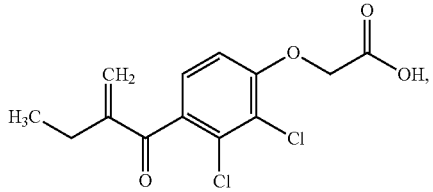 [SMILES: C=C(CC)C(=O)c1ccc(OCC(=O)O)c(Cl)c1Cl]

bezafibrate, fenofibrate, and/or griseofulvin, b) compound (II), which is ciclopirox

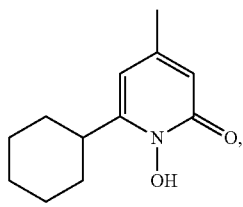

ciclopirox olamine, octopirox, and/or cinnarizine,
c) mixtures of compound (I) and compound (II),
or pharmaceutically acceptable derivatives thereof
for the manufacture of a medicament for the treatment of cancer.

In a preferred embodiment, the compositions described are used for the manufacture of a medicament for the treatment of myeloma, lymphoma and leukemia.

In a further preferred embodiment, the compositions are used for the manufacture of a medicament, wherein the composition is present in dosage unit form in the medicament.

In a further preferred embodiment, such a dosage unit form comprises
a) approximately 1 to 1000 mg of ethacrynic acid, or a pharmaceutically acceptable derivative thereof, or
b) approximately 1 to 1000 mg of ciclopirox, or a pharmaceutically acceptable derivative thereof, or
c) a mixture of 1 to 1000 mg of ethacrynic acid, or a pharmaceutically acceptable derivative thereof and 1 to 1000 mg ciclopirox, or a pharmaceutically acceptable derivative thereof,
or pharmaceutically acceptable derivatives thereof.

The present invention is further directed to a method for treating cancer in animals and humans, characterized by administering an amount sufficient to treat the cancer of a composition comprising one or more compounds selected from the group consisting of
a) compound (I) which is
   ethacrynic acid

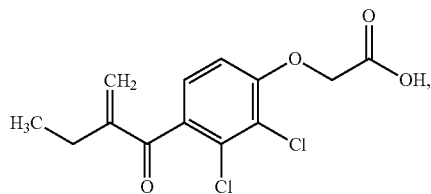 [SMILES: C=C(CC)C(=O)c1ccc(OCC(=O)O)c(Cl)c1Cl]

bezafibrate, fenofibrate, and/or griseofulvin,
b) compound (II), which is
   ciclopirox

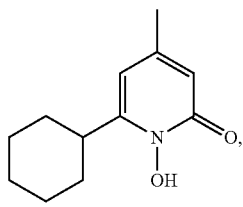

ciclopirox olamine, octopirox, and/or cinnarizine,
c) mixtures of compound (I) and compound (II),
or pharmaceutically acceptable derivatives thereof.

In a preferred embodiment, the method described above is for treating myeloma, lymphoma and leukemia.

In a further preferred embodiment, the composition used in the above-described method is adapted for oral, parenteral, rectal, nasal, vaginal, or topical administration.

In a further preferred embodiment of the above-described method
a) ethacrynic acid, or a pharmaceutically acceptable derivative thereof, is administered at a dose of about 1 to 1000 mg/kg of a bodyweight per day, or
b) ciclopirox, or a pharmaceutically acceptable derivative thereof, is administered at a dose of about 1 to 1000 mg/kg of a bodyweight per day, or
c) ethacrynic acid, or a pharmaceutically acceptable derivative thereof, is administered at a dose of about 1 to 1000 mg/kg per day in combination with the administration of ciclopirox, or a pharmaceutically acceptable derivative thereof, at a dose of about 1 to 1000 mg/kg of a bodyweight per day.

The present inventors have carried out numerous experiments to show the efficiency of ethacrynic acid and ciclopirox in the treatment of cancer. These experiments are shown in the examples further below.

The experiments shown in the examples document that the drugs EA and cic are more toxic to lymphoma—and myeloma cells than to normal PBMCs. Therefore an aim of the experiment was to find a concentration or combination of the drugs EA and cic to whose lymphoma—and myeloma cells are more sensitive than normal PBMCs. The higher the difference in comparison to the cell lines and the PBMCs the more effective would be a treatment with these drugs in cancer therapy.

The experiments carried out by the present inventors have shown that ethacrynic acid and ciclopirox in particular is a combination of these substances are effective against cancer cells.

EA as a substrate can interact with the GST which leads to a depletion of intracellular GSH. It inhibits GST by covalently binding to this enzyme (Petrini et al, 1993). The GSTs belong to a family of homo- and heterodimeric enzymes participating in the detoxification reactions of xenobiotics (Nagourney et al, 1990). GSH plays a role in regulating mutagenic mechanisms, DNA synthesis, growth, multidrug resistance and radiation resistance. As a consequence, cancer cells have in most cases higher GSH levels compared to normal cells (Estrela et al, 2006). Therefore the cell lines LAM-53, Raji and OPM-2 are more sensitive to EA exposure than normal PBMCs as reference. GST-P has other functions including non-substrate binding of steroids, bile acids, and the transcriptional regulator retinoic acid. Biosynthetic pathways of leukotriene and prostaglandin synthesis are regulated by GST isozymes. In response to DNA synthesis, GST acts as reducing agent in the thioredoxin cycle, promoting the production of deoxyriboses, the building blocks of DNA. There is evidence that EA enhances the cytotoxicity of chlorambucil. Through inhibition of GST by EA, the detoxification of chlorambucil by the cell would be impaired. Therefore, the interference in thiol metabolism and GST functions by EA was shown to be beneficial in reversing tumor resistance to anticancer drugs (Mccaughan et al, 1994; Tew et al, 1988).

At higher concentrations, EA inhibits other enzymes essential for cellular metabolism. These are sodium/potassium-dependent ATPase, glyceraldehyde phosphate, lactate, succinate, malate, and α-ketoglutarate dehydrogenases. Therefore apoptosis is induced when EA is given at lower concentrations (GST-P specific range), while at higher concentrations of EA (non-specific range), the cells undergo directly necrosis (Mccaughan et al, 1994). The maximum dosage which can be administered i.v. to a patient is about 56 µM EA (Tablets Edecrin (Ethacrynic acid) and intravenous Sodium Edecrin (Ethacrynate sodium) (2005). Merck & Co., Inc. Whitehouse Station, N.Y., USA). A dosage of 30 µM EA would be below this tolerance level. In the experiments with 30 µM EA however, there is only a significant toxicity achieved for Raji but this is by far not as effective as the usage of 10 µM cic alone.

Fast proliferating lymphoma—and myeloma cells seem to be more sensitive against the treatment with cic than normal tissue cells. Malignancy which is usually associated with a high proliferation rate might be the main target for the non-steroidal antiinflammatory drug cic. The mechanism of cic as an iron-chelator enables this drug to interrupt enzymatic reactions which depend on iron. This function blocks intracellular pathways which are necessary to proliferate and to keep the cell alive. There are a variety of proteins like heme-containing proteins, electron transport chain, microsomal electron transport proteins and enzymes like ribonucleotide reductase, prolyl hydroxylase, phenylalanine hydroxylase, thyrosine hydroxylase and aconitase inhibited if iron depletion occurs within a cell (Arredondo et al, 2005). The formation of hypusine, the stabilization of hypoxia-inducible factor 1α (HIF-1α) and the synthesis of deoxyribonucleotides from ribonucleotides by the ribonucleotide reductase (RNR) are probably the main pathways which are concerned.

A small (18 kDa) universally conserved protein eukaryotic initiation factor 5A (eIF5A) contains the polyamine-derived amino acid hypusine. The eIF5A is a ribosome-associated, mRNA-specific translation factor that stimulates ribosome function is essential for the control of cell proliferation (Clement et al, 2003). The formation of the rare amino acid hypusine occurs in two sequential post-translational modifications, where the covalent structure of genetically encoded, peptide-bound amino acids is trans-formed into novel residues (Cracchiolo et al, 2004). The first of the two enzymatic steps in hypusine formation is catalyzed by deoxyhypusine synthase. Deoxyhypusine is formed by the transfer of the aminobutyl moiety of the polyamine spermidine to the ε-amino group of a specific lysine residue in the eIF5A precursor. This formation is NAD dependent. In the second modification step, deoxyhypusine hydroxylase is involved in the hydroxylation of the side chain of this intermediate. The reaction of deoxyhypusine hydroxylase is Fe(II)-dependent and can be inhibited by the iron-chelator cic. A disruption in the synthesis of hypusine results in arrested cell proliferation (Clement et al, 2002; Clement et al, 2003). There is a reversible arrest of the cell cycle in late G1. The existence of two isoforms of eIF5A, the eIF5A-1 which is expressed and abundant in proliferating cells and eIF5A-2 whose expression is limited to specific tissues or certain cancer cell lines emphasize the role of cic as antiproliferating agent especially in lymphoma—and myeloma cell lines (Cracchiolo et al, 2004).

The HIF-1α is a heterodimeric master regulator of oxygen homeostasis in cells. The functions of protein stability and transactivation of the α-subunit of HIF-1α are controlled by iron- and oxygen dependent hydroxylation of proline and asparagine residues (Linden et al, 2003). Hypoxia and the iron-chelator cic increase the protein level of HIF-1α (Roy et al, 2004). The HIF-1 transcription factor which is degraded by the iron-dependent HIF-1α prolyl hydroxylase enzymes under normoxic conditions regulates hypoxia-induced genes. Cic acts as a lipophilic, bidentate iron-chelator which inhibits the HIF-1α prolyl hydroxylases. This leads to the inhibition of HIF-1α hydroxylation, the stabilization of HIF-1α under normoxic conditions and finally to the hypoxic response. Cic activates the HIF-1 pathway followed by the inhibition of DNA replication initiation. The accumulation of HIF-1α protein in the nucleus and the HIF-1 DNA binding as well as the activation of exogenous reporter genes reveal the potent angiogenic activity of cic (Szüts et al, 2004; Linden et al, 2003).

The enzyme RNR which exists in three classes is responsible for the synthesis and repair of DNA (Kolberg et al, 2004). It converts the ribonucleotides into deoxyribonucleotides and therefore transforms RNA building blocks into DNA building blocks. In a ribonucleotide, RNR substitutes an OH-group on the 2'-position of ribose with a hydrogen atom. This reduction mechanism involves protein radicals. The RNR consists of a larger (R1) subunit for the binding of substrates, allosteric effectors and to provide redox-active sulfhydryl groups and a smaller (R2) subunit containing a binuclear ferric iron center and a stable tyrosyl free radical. The iron center is essential for the stability of the radical and the tyrosyl free radical for the activity of RNR. Iron-chelators like cic could inhibit DNA synthesis because the RNR is the only ferriprotein in this metabolic pathway (Nordlund et al, 2006; Nyholm et al, 1993). The induction of apoptosis prevalently on lymphoma—and myeloma cell lines by cic may be due to the level of DNA synthesis. A decrease in DNA synthesis at or below a specific level might lead to processes causing cell death instead of completing DNA replication (Cory, 1988).

The maximum concentration in human systemic tolerability studies was 275 µM cic per day (Penlac (ciclopirox) Topical Solution, 8% (2005), Dermik Laboratories, Berwyn, Pa., USA). Regarding this value, a concentration of 10 µM cic would be a possible dosage.

According to the lymphoma cell lines, Raji with 21.7% relative viability after 72 h could be an opportunity for treatment against this cell type followed by LAM-53 with 32.4% and DHL-4 with 55.9% given 10 µM cic.

If DMSO is used as solvent in an end concentration of 10 µml-1, the myeloma cell line OPM-2 with a relative viability of 29.4% after 72 h could also be effectively treated with cic (10 µM). The results indicate a higher susceptibility of myeloma cells towards DMSO than lymphoma cell towards this solvent. Regarding this behaviour it was shown on mouse myeloma cells that 15% DMSO stabilized and stimulated the enzymatic activity in these cells. Furthermore, DMSO when applied between 10 and 20% (v/v) stabilized the RNA polymerase A leading to a change in template specificity predominantly to single stranded DNA (Lezius et al, 1972).

The combination of EA (30 µM) and dc (10 µM), however only for the PBMCs, was significantly more intensive in the induction of apoptosis than the concentrations of EA (30 µM) and cic (10 µM) alone. The PBMCs were the only cells for those EA exerted a stronger decrease in relative viability than cic regarded to the cell lines tested. EA might have bound to GSH to disturb the detoxification mechanism of the cell. In this case EA contributed in making the cell more sensitive to cic. This could have let to a complementation of both drugs EA together with cic given in combination. An enhancing property of EA if given in combination with another drug was already shown for drugs such as doxorubicin, chorambucil, carmustine and nitrogen mustard (Nagourney et al, 1990; Petrini et al, 1993).

If cic (10 µM) was much more effective than EA (30 µM), the drugs EA and cic in combination would exert a weaker effect than cic (10 µM) alone, especially for Raji having the highest proliferation rate of all tested cell lines with a doubling time of 24-36 h, compared with DHL-4 (40 h) and OPM-2 (50-60 h) (DSMZ). Cic as iron chelator which inhibits the synthesis of deoxyribonucleotides, the rate-limiting step in DNA synthesis, could be regarded as major active compound in fast proliferating cells between EA and cic. A diminishing effect of the combination EA (30 µM) together with cic (10 µM) by binding of the drugs by each other would make no sense because of the additive effect of the combination for the PBMCs. Therefore an inhibition of one drug for the other could give rise to the drugs when they are expressed in their reactive forms. This means if EA would have bound GSH depending on the GSH level in a cell and cic would have formed its chelate complex with iron depending on the expression of biochemical pathways in a cell which require iron for stabilization of their enzymes. The level of activation of both substances could have influence of an inhibitory or enhancing effect for the combination concerning the property of the cell line. EA as an aryl halide can undergo nucleophilic or electrophilic substitution reactions. There is evidence that EA substitutes its chloride atom at 3' position by methyl, bromide, or fluoride. This is necessary for the inhibition of GST P1-1 activity (Zhao et al, 2005). Besides building a complex with GSH, EA might target the positively charged chelate complex of cic with iron by its two partial negatively charged chloride atoms bound on the benzene ring. This would be the case if EA alone is less toxic to the cell line than cic alone. If EA would bound to a higher degree on GSH molecules on the 3' position, the attraction towards the chelate complex might be weaker due to steric hinderence. In fast proliferating cells to those dc is much stronger in the induction of apoptosis than EA, the drug EA may inhibit the formation of the chelate complex of iron and cic and in this way the cell can regain iron. It was found out that the inhibition of cell growth by iron-chelators which remove all accessible iron from the medium is reversible on the addition of iron (Nyholm et al, 1993).

Cic seems to be an indicator of the cell proliferation rate because of the inhibition of hypusine formation and the synthesis of deoxyribonucleotides. The effect of EA probably depends on the expression of GST, especially of the GST P1-1 in lymphoma—and myeloma cell lines. According to the results of the experiment, the dosage of 30 µM EA is nearer to the critical level of 56 µM EA than 10 µM cic in respect to 275 µM dc. This might indicate that cic would either inhibit a biochemical mechanism which is specific for lymphoma— and myeloma cells and predominantly susceptible to cic or inhibit a variety of mechanisms characteristic for a higher expression to those cells. However, an order of mechanisms inhibited by cic and their level of susceptibility cannot be determined in this experiment.

The formation of the EA-GSH complex by EA probably does not significantly induce apoptosis which might be the case when excess unbound EA interrupts intracellular biochemical pathways. If a high level of unbound EA remains in the cell, an interaction with the iron chelate complex of cic could lead to a less apoptotic effect of the combination EA (30 µM) and dc (10 µM) compared to a high apoptotic effect of EA (30 µM) and cic (10 µM) alone in the Raji cells.

The supposition that free radicals are formed when iron chelation takes place which could be detoxified by GSH might reveal that this effect would be relatively weak because an enhancing property of EA together with cic cannot be observed if cic alone exerts a strong inhibitory effect.

The invention described above is further illustrated by the following examples:

Example 1

Analysis of the Effect of EA and cic on Cell Lines and PBMCs by FACS Analysis

Titration of EA and cic on the cell lines and PBMCs revealed that 30 µM EA and 10 µM cic are the most representative concentrations. The effect of DMSO as a toxic solvent was observed in the myeloma cell line OPM-2.

Figure 5:
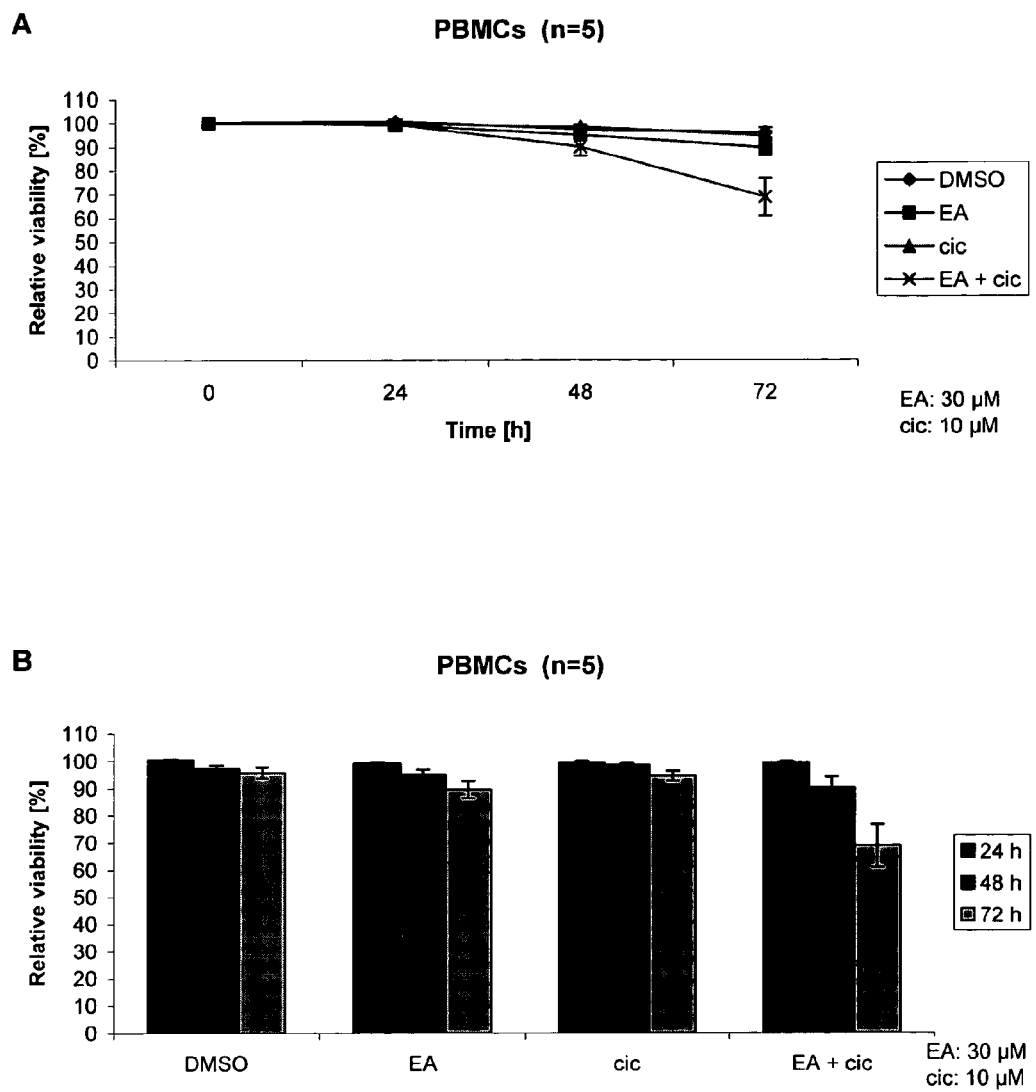
FIG. 5 shows the relative viability of the PBMCs exposed to EA (30 µM), cic (10 µM) and the combination of EEA (30 µM) together with cic (10 µM). DMSO, the solvent of EA and cic, was given to the PBMCs in a ratio of 1:100, as control. The values are related to the culture-control and expressed as mean±standard error of the mean (SEM) taken from 5 separate measurements.
Figure 6:
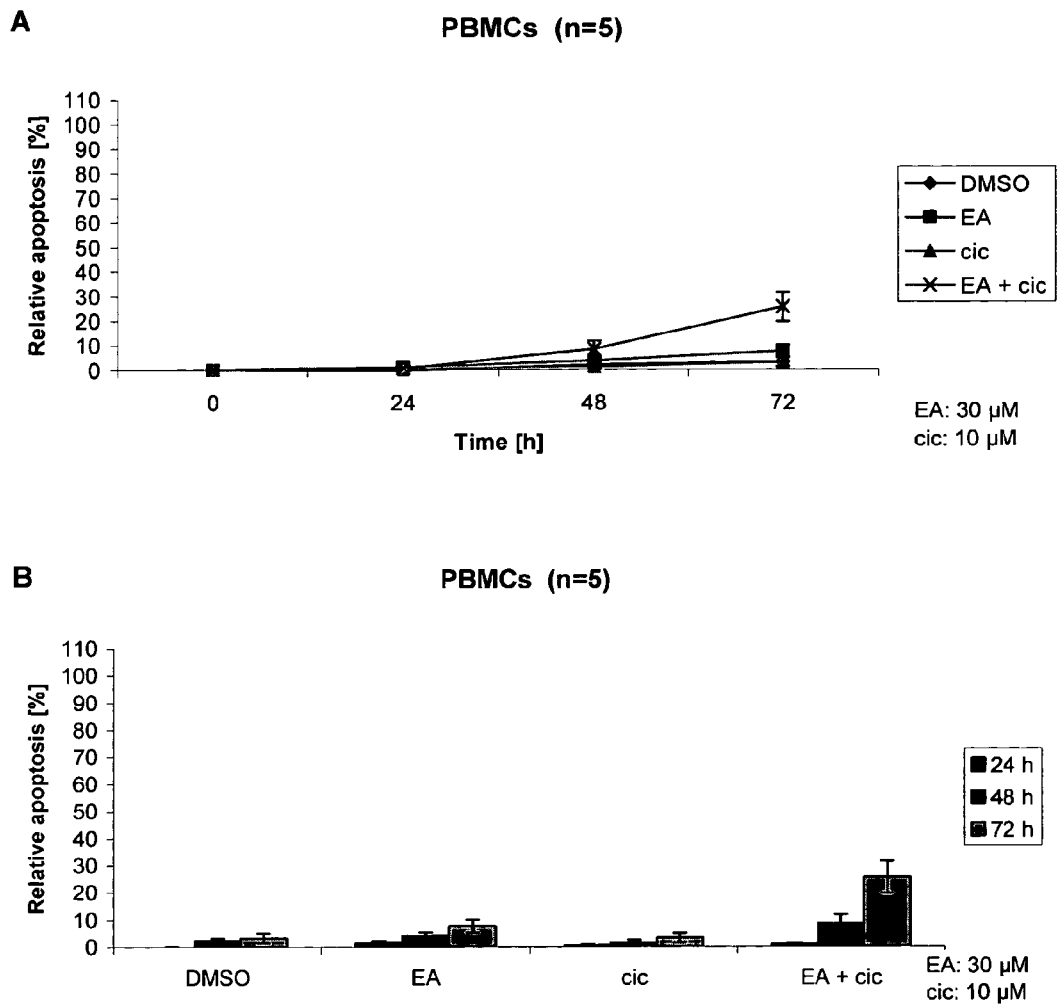
FIG. 6 shows the relative apoptosis of the PBMCs exposed to EA (30 μM), cic (10 μM) and the combination of EA (30 μM) together with cic (10 μM). DMSO, the solvent of EA and cic, was given to the PBMCs in a ratio of 1:100, as control. The values are related to the culture-control and expressed as mean±standard error of the mean (SEM) taken from 5 separate measurements.

The peripheral blood lymphocytes (PBLs) out of the PBMCs were selected for the FACS analysis (FIG. 5). A toxicity of the cells induced a shift from viable cells to apoptotic cells (FIG. 6, 7). If the drug or its concentration is very toxic, the cells appear addition-ally in a higher extent necrotic.

Figure 2:
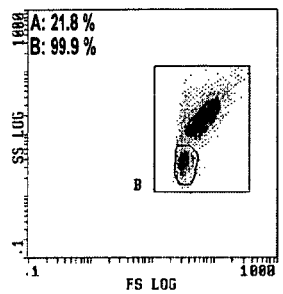
FIG. 2 shows FACS data of the culture-control taken from the PBMCs and the cell lines LAM-53, DHL-4, OPM-2 and Raji, measured after 72 h. The plots represent the cell population in the Side-Scatter (SS) against Forward-Scatter (FS) scheme and the setting of the gates.
Figure 2:
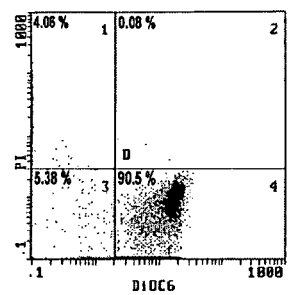
Figure 2:
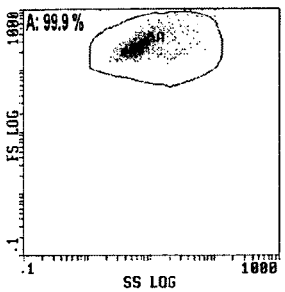
Figure 2:
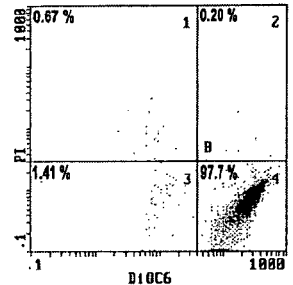
Figure 2:
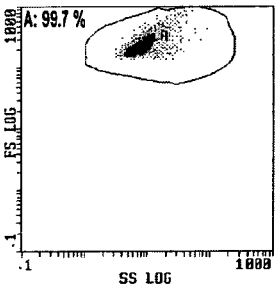
Figure 2:
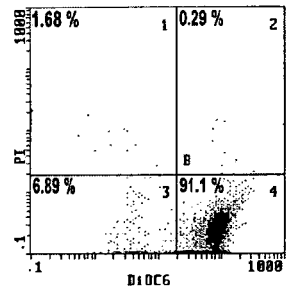
Figure 2:
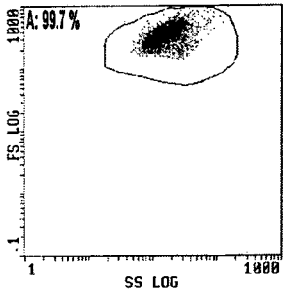
Figure 2:
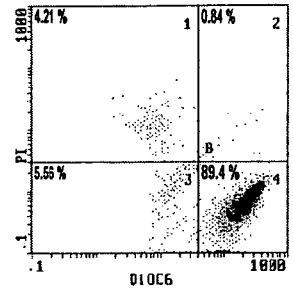
Figure 2:
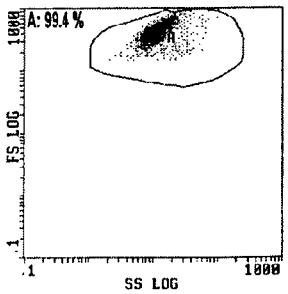
Figure 2:
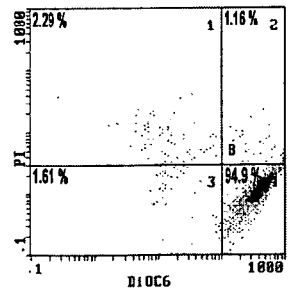

FIG. 2 shows FACS data of the culture-control taken from the PBMCs and the cell lines LAM-53, DHL-4, OPM-2 and Raji, measured after 72 h. The plots represent the cell population in the Side-Scatter (SS) against Forward-Scatter (FS) scheme and the setting of the gates.

Figure 3:
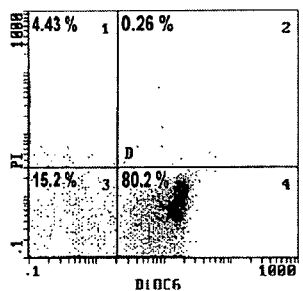
FIG. 3 shows FACS data of the PBMCs and the cell lines LAM-53, DHL-4, OPM-2 and Raji measured after 72 h. (A) The DMSO-control. (B) The exposure to EA (30 µM) and cic (10 µM).
Figure 3:
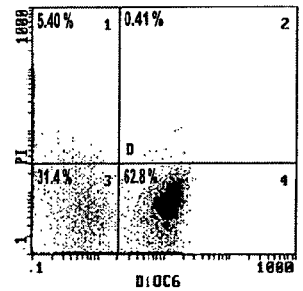
Figure 3:
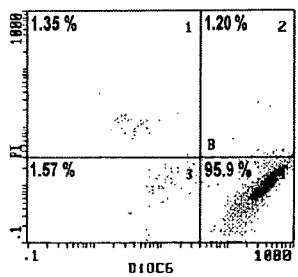
Figure 3:
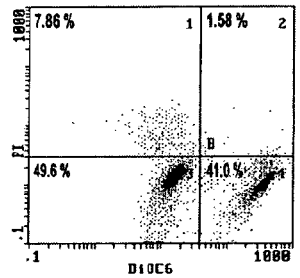
Figure 3:
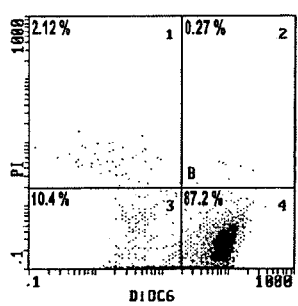
Figure 3:
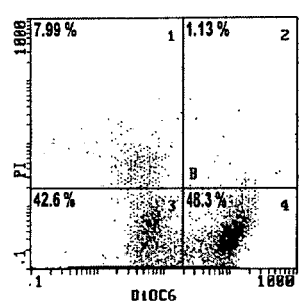
Figure 3:
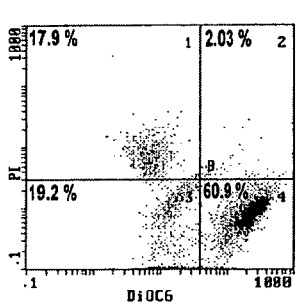
Figure 3:
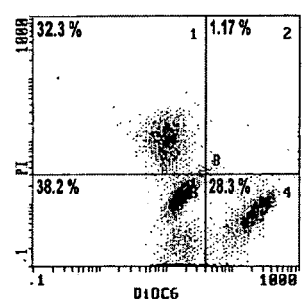
Figure 3:
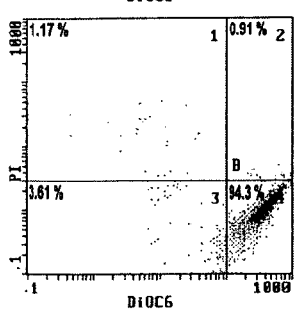
Figure 3:
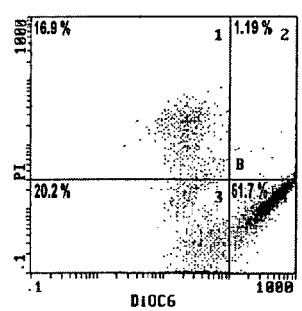

FIG. 3 shows FACS data of the PBMCs and the cell lines LAM-53, DHL-4, OPM-2 and Raji measured after 72 h. (A) The DMSO-control. (B) The exposure to EA (30 µM) and dc (10 µM).

Figure 4:
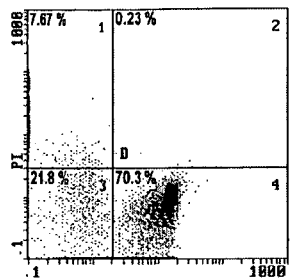
FIG. 4 shows FACS data of the PBMCs and the cell lines LAM-53, DHL-4, OPM-2 and Raji measured after 72 h. (A) The cells treated with EEA (30 µM). (B) The exposure to cic (10 µM).
Figure 4:
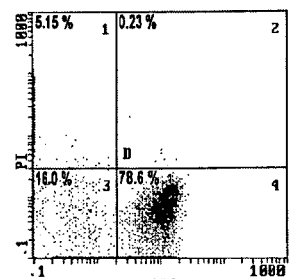
Figure 4:
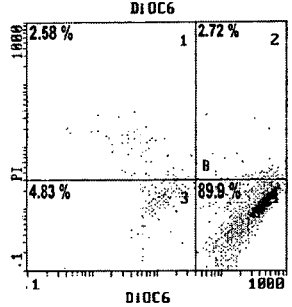
Figure 4:
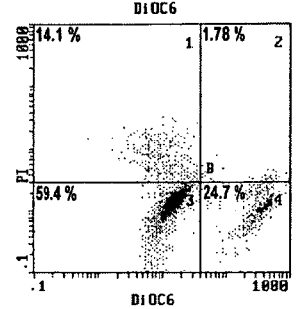
Figure 4:
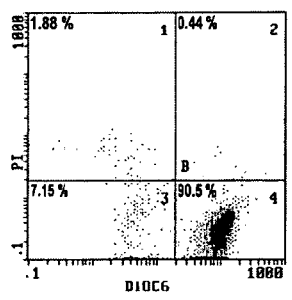
Figure 4:
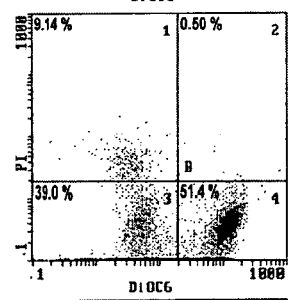
Figure 4:
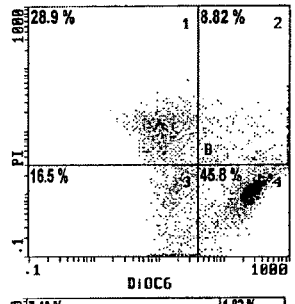
Figure 4:
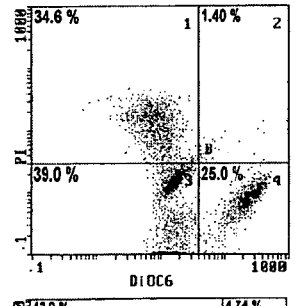
Figure 4:
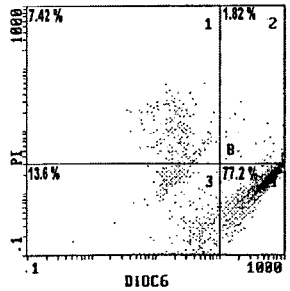
Figure 4:
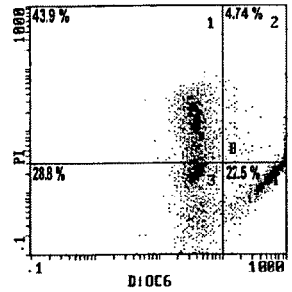

FIG. 4 shows FACS data of the PBMCs and the cell lines LAM-53, DHL-4, OPM-2 and Raji measured after 72 h. (A) The cells treated with EA (30 µM). (B) The exposure to cic (10 µM).

Example 2

Relative Viability of PBMCs Exposed to EA, cic and the Combination of EA Together with cic The relative viability for the PBMCs as control was less for EA (30 µM) with 89.5 than cic (10 µM) with 94.4% after 72 h (FIG. 5, Tab. 1). An enhancing decrease, especially after 72 h, could be found for the combination of EA (30 µM) together with cic (10 µM) reaching a final value of 68.7%.

FIG. 5 shows the relative viability of the PBMCs exposed to EA (30 µM), cic (10 µM) and the combination of EA (30 µM) together with cic (10 µM). DMSO, the solvent of EA and cic, was given to the PBMCs in a ratio of 1:100, as control. The values are related to the culture-control and expressed as mean±standard error of the mean (SEM) taken from 5 separate measurements. In FIG. 5 (A) samples were measured after 24, 48 and 72 h. After 0 h, the time of execution, the relative viability was defined as 100° A) for all samples. In FIG. 5 (B) the relative viability values for the samples measured after 24, 48 and 72 h.

TABLE 1

| | | | | | | | | |
|---|---|---|---|---|---|---|---|---|
| The relative viability for the PBMCs given in %. | | | | | | | | |
| Culture = 100% | | | | | | | | |
| Time [h]: | DMSO: | ±SEM: | 30 µM EA: | ±SEM: | P-value: | 10 µM cic: | ±SEM: | P-value: |
| 0 | 100.0 | 0.0 | 100.0 | 0.0 | — | 100.0 | 0.0 | — |
| 24 | 100.5 | 0.3 | 98.9 | 0.7 | 0.071 | 99.3 | 0.6 | 0.120 |
| 48 | 97.2 | 1.2 | 94.9 | 1.9 | 0.335 | 98.3 | 0.8 | 0.482 |
| 72 | 95.7 | 2.1 | 89.5 | 3.1 | 0.139 | 94.4 | 1.8 | 0.650 |
| Culture = 100% | | | 30 µM EA + | | | | | |
| Time [h]: | DMSO: | ±SEM: | 10 µM cic: | ±SEM: | P-value: | | | |
| 0 | 100.0 | 0.0 | 100.0 | 0.0 | — | | | |
| 24 | 100.5 | 0.3 | 99.2 | 0.6 | 0.093 | | | |
| 48 | 97.2 | 1.2 | 90.0 | 4.0 | 0.119 | | | |
| 72 | 95.7 | 2.1 | 68.7 | 7.9 | 0.011 | | | |

The relative apoptosis was highest after 72 h for the combination of EA (30 µM) together with cic (10 µM) represented by a value of 25.6% followed by EA (30 µM) with 7.6% (FIG. 6, Tab. 2). DMSO and cic (10 µM) had similar values namely 3.2% and 3.3 after 72 h.

FIG. 6 shows the relative apoptosis of the PBMCs exposed to EA (30 µM), cic (10 µM) and the combination of EA (30 µM) together with cic (10 µM). DMSO, the solvent of EA and cic, was given to the PBMCs in a ratio of 1:100, as control. The values are related to the culture-control and expressed as mean±standard error of the mean (SEM) taken from 5 separate measurements. In FIG. 6 (A) samples were measured after 24, 48 and 72 h. After 0 h, the time of execution, the relative apoptosis was defined as 0% for all samples. In FIG. 6 (B) the relative apoptosis values for the samples measured after 24, 48 and 72 h.

Figure 7:
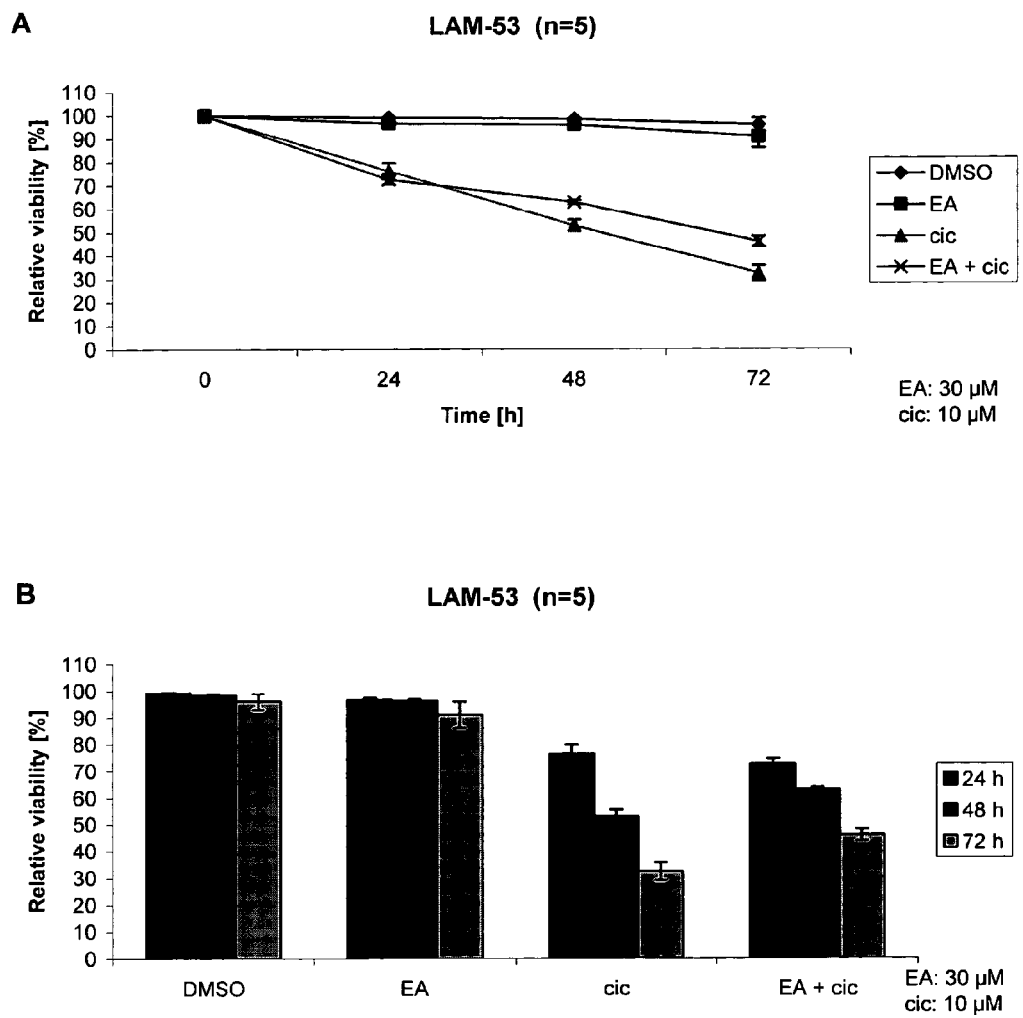
FIG. 7 shows the relative viability of the cell line LAM-53 exposed to EA (30 μM), cic (10 μM) and the combination of EEA (30 μM) together with cic (10 DMSO, the solvent of EA and cic, was given to the cell line LAM-53 in a ratio of 1:100, as control. The values are related to the culture-control and expressed as mean±standard error of the mean (SEM) taken from 5 separate measurements.

76.2% after 48 h and finally reaching 32.4% after 72 h (FIG. 7, Tab. 3). For EA (30 µM), only less decrease was observed after 72 h with 91.0 compared to the DMSO-control with 96.0%. The combination of EA (30 µM) together with cic (10 µM) first decreased in a similar rate compared to cic (10 µM) alone until 24 h after exposure with 72.5%. On the following time the relative viability for the combination decreased more slowly than cic (10 µM) alone to a final value of 46.0% after 72 h. In comparison to the PBMCs, cic (10 µM) was most efficient after 72 h with a relative viability of 32.4% for LAM-53 and a value of 94.4% for the PBMCs.

FIG. 7 shows the relative viability of the cell line LAM-53 exposed to EA (30 µM), dc (10 µM) and the combination of EA (30 µM) together with cic (10 µM). DMSO, the solvent of EA and cic, was given to the cell line LAM-53 in a ratio of

TABLE 2

| | | | | | | | | |
|---|---|---|---|---|---|---|---|---|
| The relative apoptosis for the PBMCs given in %. | | | | | | | | |
| Culture = 0% | | | | | | | | |
| Time [h]: | DMSO: | ±SEM: | 30 µM EA: | ±SEM: | P-value: | 10 µM cic: | ±SEM: | P-value: |
| 0 | 0.0 | 0.0 | 0.0 | 0.0 | — | 0.0 | 0.0 | — |
| 24 | −0.2 | 0.3 | 1.3 | 0.9 | 0.141 | 0.4 | 0.4 | 0.235 |
| 48 | 2.2 | 1.0 | 3.9 | 1.4 | 0.348 | 1.4 | 1.0 | 0.588 |
| 72 | 3.2 | 1.8 | 7.6 | 2.4 | 0.183 | 3.3 | 1.8 | 0.988 |
| Culture = 0% | | | 30 µM EA + | | | | | |
| Time [h]: | DMSO: | ±SEM: | 10 µM cic: | ±SEM: | P-value: | | | |
| 0 | 0.0 | 0.0 | 0.0 | 0.0 | — | | | |
| 24 | −0.2 | 0.3 | 0.8 | 0.4 | 0.097 | | | |
| 48 | 2.2 | 1.0 | 8.4 | 3.5 | 0.124 | | | |
| 72 | 3.2 | 1.8 | 25.6 | 5.9 | 0.007 | | | |

Example 3

Relative Viability of the Cell Line LAM-53 Exposed to EA, cic and the Combination of EA Together with cic The relative viability of the cell line LAM-53 decreased almost constantly for dc (10 µM) from 100% after 0 h, to 1:100, as control. The values are related to the culture-control and expressed as mean±standard error of the mean (SEM) taken from 5 separate measurements. In FIG. 7 (A) samples were measured after 24, 48 and 72 h. After 0 h, the time of execution, the relative viability was defined as 100% for all samples. In FIG. 7 (B) the relative viability values for the samples measured after 24, 48 and 72 h.

TABLE 3

The relative viability for the cell line LAM-53 given in %.

| | Culture = 100% | | | | | | | |
|---|---|---|---|---|---|---|---|---|
| Time [h]: | DMSO: | ±SEM: | 30 µM EA: | ±SEM: | P-value: | 10 µM cic: | ±SEM: | P-value: |
| 0 | 100.0 | 0.0 | 100.0 | 0.0 | — | 100.0 | 0.0 | — |
| 24 | 99.2 | 0.2 | 96.7 | 0.8 | 0.017 | 76.2 | 3.5 | 0.000 |
| 48 | 98.6 | 0.4 | 96.2 | 0.7 | 0.015 | 52.9 | 2.4 | 0.000 |
| 72 | 96.0 | 3.0 | 91.0 | 4.9 | 0.404 | 32.4 | 3.3 | 0.000 |

| | Culture = 100% | | 30 µM EA + | | |
|---|---|---|---|---|---|
| Time [h]: | DMSO: | ±SEM: | 10 µM cic: | ±SEM: | P-value: |
| 0 | 100.0 | 0.0 | 100.0 | 0.0 | — |
| 24 | 99.2 | 0.2 | 72.5 | 2.0 | 0.000 |
| 48 | 98.6 | 0.4 | 62.9 | 0.9 | 0.000 |
| 72 | 96.0 | 3.0 | 46.0 | 2.1 | 0.000 |

Figure 8:
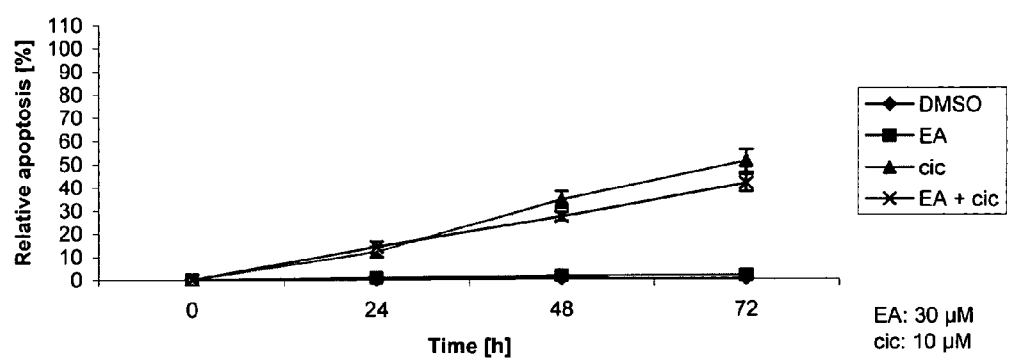
FIG. 8 shows the relative apoptosis of the cell line LAM-53 exposed to EEA (30 μM), cic (10 μM) and the combination of EEA (30 μM) together with cic (10 μM). DMSO, the solvent of EEA and cic, was given to the cell line LAM-53 in a ratio of 1:100, as control. The values are related to the culture-control and expressed as mean±standard error of the mean (SEM) taken from 5 separate measurements.
Figure 8:
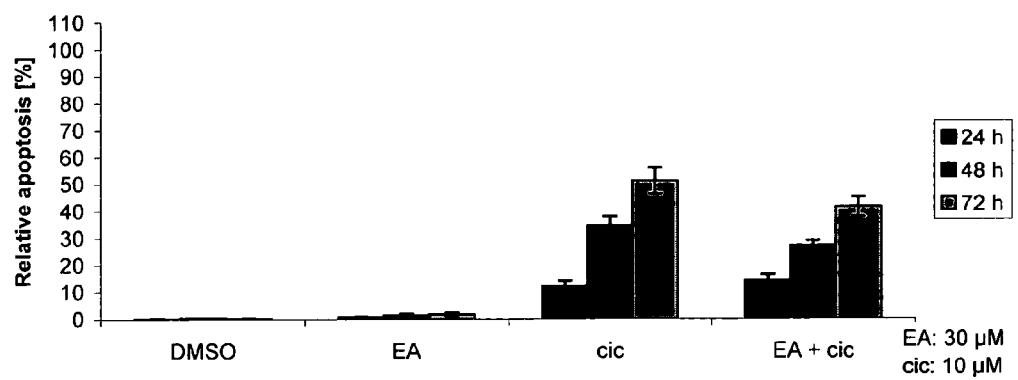

The relative apoptosis for LAM-53 increased for cic (10 µM) from 12.2% after 24 h to 34.4% after 48 h and reaching a final value of 51.2% after 72 h (FIG. 8, Tab. 4). For EA (30 µM) there was only a little increase observed having the highest value after 72 h with 1.8%. The combination of EA (30 µM) together with cic (10 µM) increased constantly over the 72 h time period from 14.2% after 24 h to 41.6%. The solvent DMSO can be mentioned as non-toxic to LAM-53.

Figure 9:
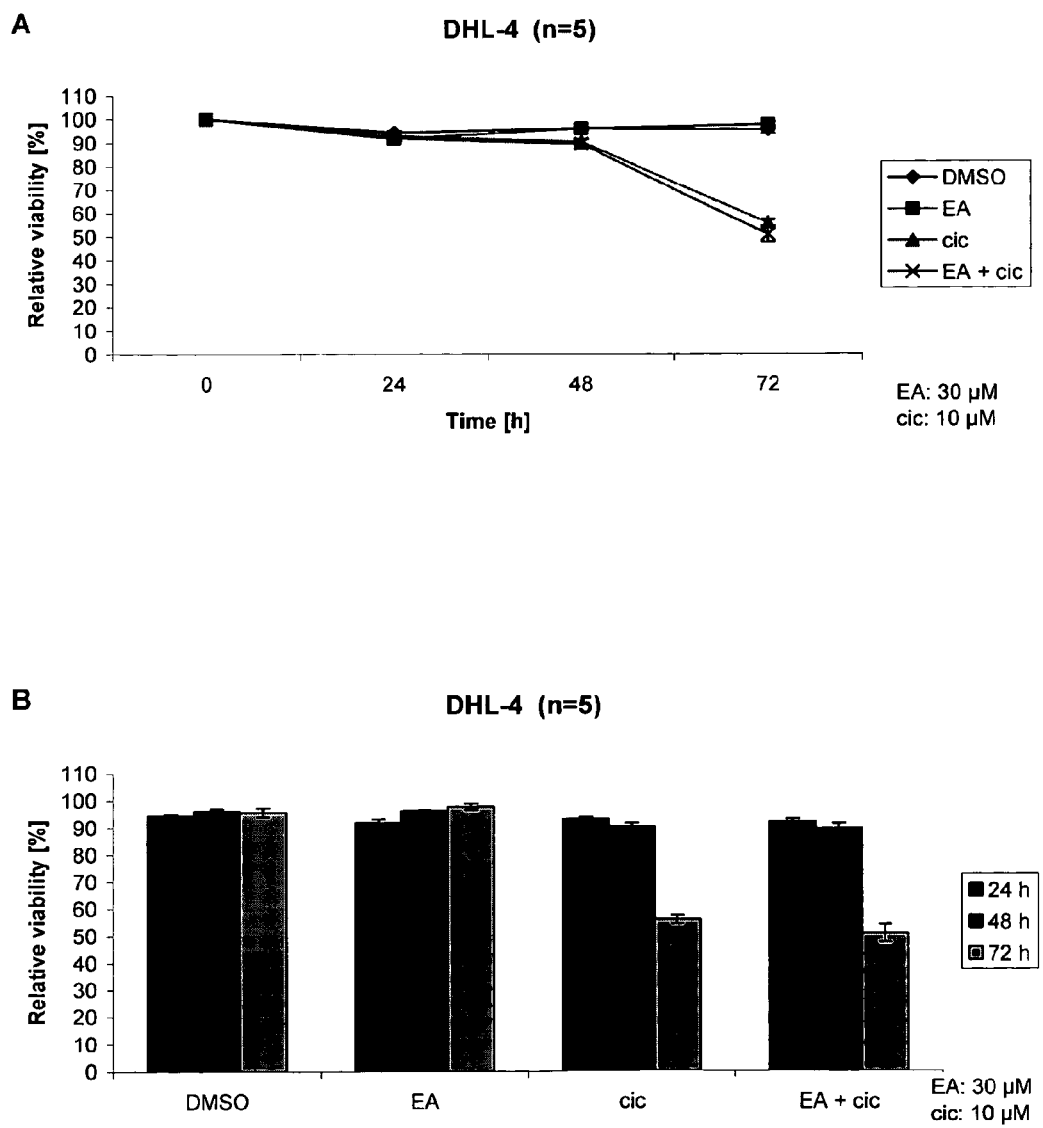
FIG. 9 shows the relative viability of the cell line DHL-4 exposed to EEA (30 μM), cic (10 μM) and the combination of EEA (30 together with cic (10 DMSO, the solvent of EA and cic, was given to the cell line DHL-4 in a ratio of 1:100, as control. The values are related to the culture-control and expressed as mean±standard error of the mean (SEM) taken from 5 separate measurements.

FIG. 8 shows the relative apoptosis of the cell line LAM-53 exposed to EA (30 µM), cic (10 µM) and the combination of EA (30 µM) together with cic (10 µM). DMSO, the solvent of EA and cic, was given to the cell line LAM-53 in a ratio of 1:100, as control. The values are related to the culture-control and expressed as mean±standard error of the mean (SEM) taken from 5 separate measurements. In FIG. 8 (A) samples were measured after 24, 48 and 72 h. After 0 h, the time of execution, the relative apoptosis was defined as 0% for all samples. In FIG. 8 (B) the relative apoptosis values for the samples measured after 24, 48 and 72 h.

bination of EA (30 µM) together with cic (10 µM) between 48 h and 72 h (FIG. 9, Tab. 5). The minimum value after 72 h for cic (10 µM) was 55.9 and for the combination of EA (30 µM) together with cic (10 µM) a relative viability of 50.8% was detected. The concentration of EA (30 µM) alone had a relative viability less than the DMSO-control after 24 h but changed into a little increase in relative viability compared to the DMSO-control up to 72 h. In comparison to the PBMCs, the highest difference in relative viability was achieved for cic (10 µM) after 72 h with 55.9% for DHL-4 and 94.4% for the PBMCs.

FIG. 9 shows the relative viability of the cell line DHL-4 exposed to EA (30 µM), cic (10 µM) and the combination of EA (30 µM) together with cic (10 µM). DMSO, the solvent of

TABLE 4

The relative apoptosis for the cell line LAM-53 given in %.

| | Culture = 0% | | | | | | | |
|---|---|---|---|---|---|---|---|---|
| Time [h]: | DMSO: | ±SEM: | 30 µM EA: | ±SEM: | P-value: | 10 µM cic: | ±SEM: | P-value: |
| 0 | 0.0 | 0.0 | 0.0 | 0.0 | — | 0.0 | 0.0 | — |
| 24 | 0.1 | 0.2 | 0.7 | 0.4 | 0.195 | 12.2 | 2.1 | 0.000 |
| 48 | 0.4 | 0.1 | 1.5 | 0.5 | 0.079 | 34.4 | 3.6 | 0.000 |
| 72 | 0.2 | 0.1 | 1.8 | 0.6 | 0.035 | 51.2 | 4.9 | 0.000 |

| | Culture = 0% | | 30 µM EA + | | |
|---|---|---|---|---|---|
| Time [h]: | DMSO: | ±SEM: | 10 µM cic: | ±SEM: | P-value: |
| 0 | 0.0 | 0.0 | 0.0 | 0.0 | — |
| 24 | 0.1 | 0.2 | 14.2 | 2.3 | 0.000 |
| 48 | 0.4 | 0.1 | 27.2 | 1.8 | 0.000 |
| 72 | 0.2 | 0.1 | 41.6 | 3.7 | 0.000 |

Example 4

The Relative Viability of the Cell Line DHL-4 Exposed to EA (30 µM), cic (10 µM) and the Combination of EA (30 µM) Together with cic (10 µM)

The most significant decrease in relative viability for the cell line DHL-4 was obtained for cic (10 µM) and the com- EA and cic, was given to the cell line DHL-4 in a ratio of 1:100, as control. The values are related to the culture-control and expressed as mean±standard error of the mean (SEM) taken from 5 separate measurements. In FIG. 9 (A) samples were measured after 24, 48 and 72 h. After 0 h, the time of execution, the relative viability was defined as 100% for all samples. In FIG. 9 (B) the relative viability values for the samples measured after 24, 48 and 72 h.

TABLE 5

The relative viability for the cell line DHL-4 given in %.

| | Culture = 100% | | | | | | | |
|---|---|---|---|---|---|---|---|---|
| Time [h]: | DMSO: | ±SEM: | 30 µM EA: | ±SEM: | P-value: | 10 µM cic: | ±SEM: | P-value: |
| 0 | 100.0 | 0.0 | 100.0 | 0.0 | — | 100.0 | 0.0 | — |
| 24 | 94.3 | 0.7 | 91.7 | 1.3 | 0.125 | 93.0 | 0.6 | 0.218 |
| 48 | 95.9 | 0.8 | 96.0 | 0.3 | 0.929 | 90.3 | 1.2 | 0.005 |
| 72 | 95.5 | 1.6 | 97.6 | 1.1 | 0.337 | 55.9 | 1.6 | 0.000 |
| | Culture = 100% | | 30 µM EA + | | | | | |
| Time [h]: | DMSO: | ±SEM: | 10 µM cic: | ±SEM: | P-value: | | | |
| 0 | 100.0 | 0.0 | 100.0 | 0.0 | — | | | |
| 24 | 94.3 | 0.7 | 92.0 | 1.1 | 0.118 | | | |
| 48 | 95.9 | 0.8 | 89.4 | 2.0 | 0.015 | | | |
| 72 | 95.5 | 1.6 | 50.8 | 3.3 | 0.000 | | | |

Figure 10:
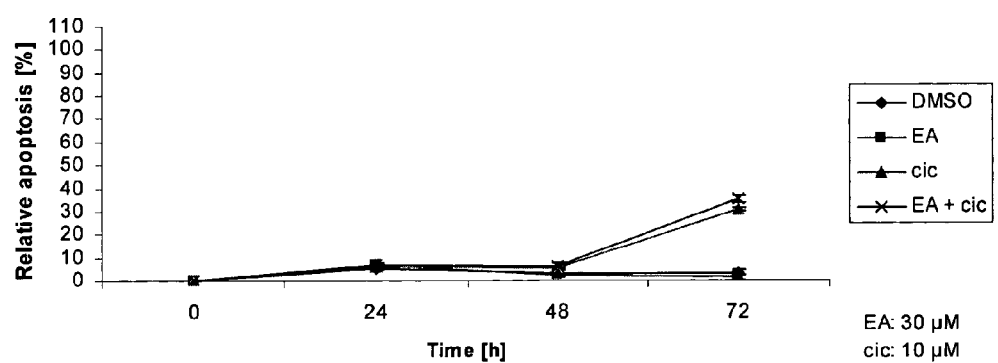
FIG. 10 shows the relative apoptosis of the cell line DHL-4 exposed to EA (30 μM), cic (10 μM) and the combination of EA (30 μM) together with cic (10 μM). DMSO, the solvent of EA and cic, was given to the cell line DHL-4 in a ratio of 1:100, as control. The values are related to the culture-control and expressed as mean±standard error of the mean (SEM) taken from 5 separate measurements.
Figure 10:
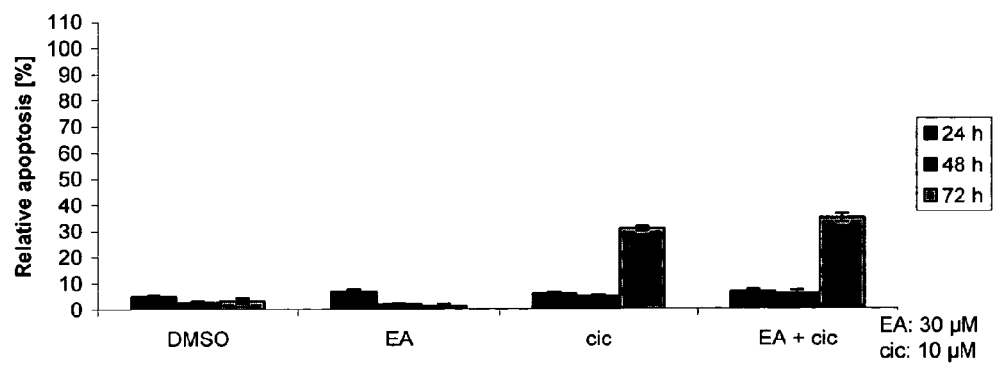

The highest increase in relative apoptosis for DHL-4 was reached after 72 h with 34.9 for the combination of EA (30 µM) together with cic (10 µM) followed by cic (10 µM) with a value of 30.8% (FIG. 10, Tab. 6). For DMSO, the highest increase in relative apoptosis was already induced after 24 h with 5.0%.

FIG. 10 shows the relative apoptosis of the cell line DHL-4 exposed to EA (30 µM), cic (10 µM) and the combination of EA (30 µM) together with cic (10 µM). DMSO, the solvent of EA and cic, was given to the cell line DHL-4 in a ratio of 1:100, as control. The values are related to the culture-control and expressed as mean±standard error of the mean (SEM) taken from 5 separate measurements. In FIG. 10 (A) samples were measured after 24, 48 and 72 h. After 0 h, the time of execution, the relative apoptosis was defined as 0% for all samples. In FIG. 10 (B) the relative apoptosis values for the samples measured after 24, 48 and 72 h.

Figure 11:
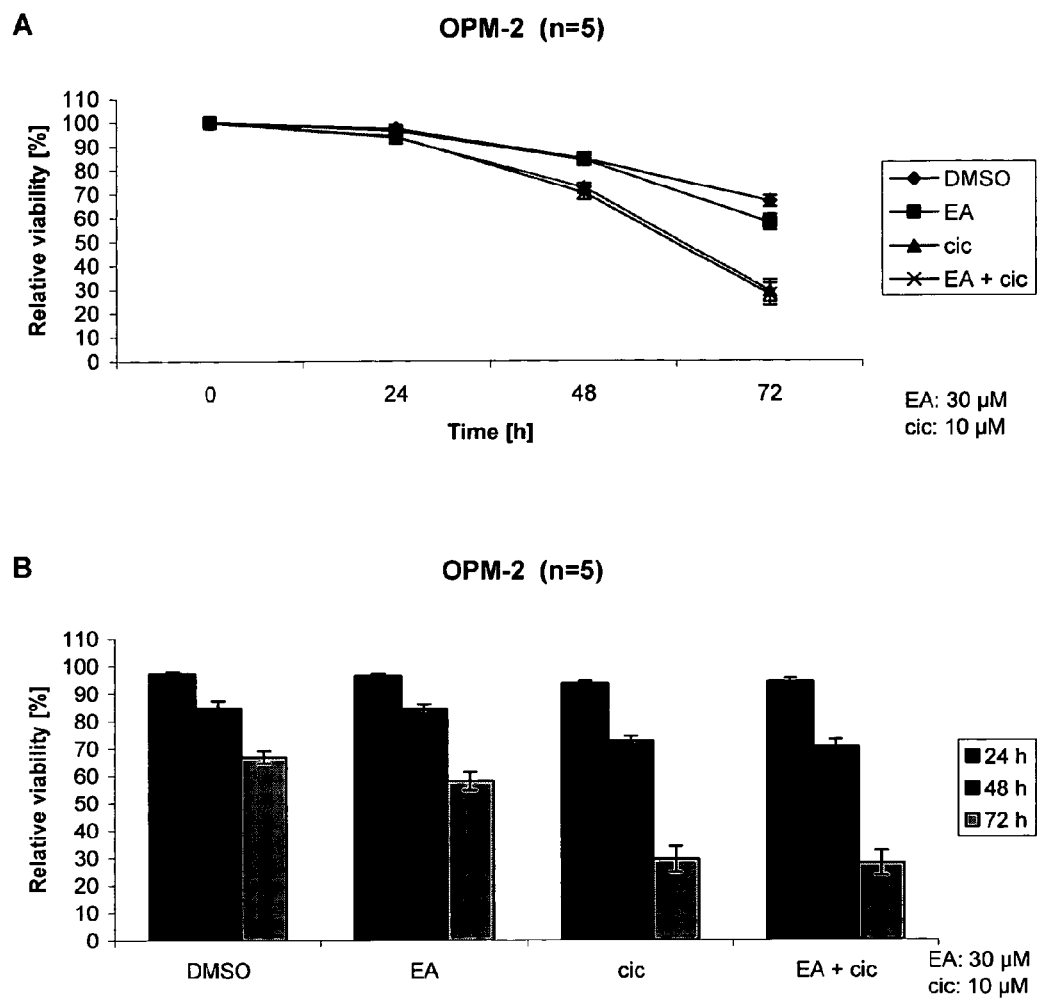
FIG. 11 shows the relative viability of the cell line OPM-2 exposed to EA (30 μM), cic (10 μM) and the combination of EA (30 μM) together with cic (10 μM). DMSO, the solvent of EA and cic, was given to the cell line OPM-2 in a ratio of 1:100, as control. The values are related to the culture-control and expressed as mean±standard error of the mean (SEM) taken from 5 separate measurements.

66.8% (FIG. 11, Tab. 7). The concentration of EA (30 µM) behaved similar to the DMSO-control from 0 h to 48 h and decreased to a value of 58.0 after 72 h. For cic (10 µM) and the combination of EA (30 µM) together with cic (10 µM) the values decreased logarithmically over the 72 h and they were very close to each other. The relative viability values for cic (10 µM) with 29.4% after 72 h and the combination of EA (30 µM) together with cic (10 µM) having 27.9% after 72 h were under those of EA (30 µM) and the DMSO-control.

FIG. 11 shows the relative viability of the cell line OPM-2 exposed to EA (30 µM), cic (10 µM) and the combination of EA (30 µM) together with cic (10 µM). DMSO, the solvent of EA and cic, was given to the cell line OPM-2 in a ratio of 1:100, as control. The values are related to the culture-control and expressed as mean±standard error of the mean (SEM) taken from 5 separate measurements. In FIG. 11 (A) samples were measured after 24, 48 and 72 h. After 0 h, the time of execution, the relative viability was defined as 100% for all samples. In FIG. 11 (B) the relative viability values for the samples measured after 24, 48 and 72 h.

TABLE 6

The relative apoptosis for the cell line DHL-4 given in %.

| | Culture = 0% | | | | | | | |
|---|---|---|---|---|---|---|---|---|
| Time [h]: | DMSO: | ±SEM: | 30 µM EA: | ±SEM: | P-value: | 10 µM cic: | ±SEM: | P-value: |
| 0 | 0.0 | 0.0 | 0.0 | 0.0 | — | 0.0 | 0.0 | — |
| 24 | 5.0 | 0.5 | 6.7 | 1.0 | 0.170 | 5.8 | 0.6 | 0.324 |
| 48 | 2.6 | 0.6 | 2.0 | 0.3 | 0.408 | 5.0 | 0.5 | 0.018 |
| 72 | 3.3 | 1.1 | 1.2 | 0.9 | 0.182 | 30.8 | 0.9 | 0.000 |
| | Culture = 0% | | 30 µM EA + | | | | | |
| Time [h]: | DMSO: | ±SEM: | 10 µM cic: | ±SEM: | P-value: | | | |
| 0 | 0.0 | 0.0 | 0.0 | 0.0 | — | | | |
| 24 | 5.0 | 0.5 | 6.6 | 0.9 | 0.148 | | | |
| 48 | 2.6 | 0.6 | 5.9 | 1.3 | 0.055 | | | |
| 72 | 3.3 | 1.1 | 34.9 | 1.6 | 0.000 | | | |

Example 5

The Relative Viability of the Cell Line OPM-2 Exposed to EA (30 µM), cic (10 µM) and the Combination of EA (30 µM) Together with cic (10 µM)

The myeloma cell line OPM-2 had a decrease in relative viability for the DMSO-control from 0 h to 72 h down to

TABLE 7

The relative viability for the cell line OPM-2 given in %.

Culture = 100%

| Time [h]: | DMSO: | ±SEM: | 30 μM EA: | ±SEM: | P-value: | 10 μM cic: | ±SEM: | P-value: |
|---|---|---|---|---|---|---|---|---|
| 0 | 100.0 | 0.0 | 100.0 | 0.0 | — | 100.0 | 0.0 | — |
| 24 | 97.2 | 0.9 | 96.4 | 0.7 | 0.507 | 93.6 | 0.9 | 0.020 |
| 48 | 84.6 | 2.7 | 84.2 | 1.8 | 0.909 | 72.5 | 1.8 | 0.005 |
| 72 | 66.8 | 2.3 | 58.0 | 3.3 | 0.060 | 29.4 | 4.7 | 0.000 |

| | Culture = 100% | | 30 μM EA + | | |
|---|---|---|---|---|---|
| Time [h]: | DMSO: | ±SEM: | 10 μM cic: | ±SEM: | P-value: |
| 0 | 100.0 | 0.0 | 100.0 | 0.0 | — |
| 24 | 97.2 | 0.9 | 94.1 | 1.3 | 0.077 |
| 48 | 84.6 | 2.7 | 70.3 | 2.7 | 0.006 |
| 72 | 66.8 | 2.3 | 27.9 | 4.6 | 0.000 |

Figure 12:
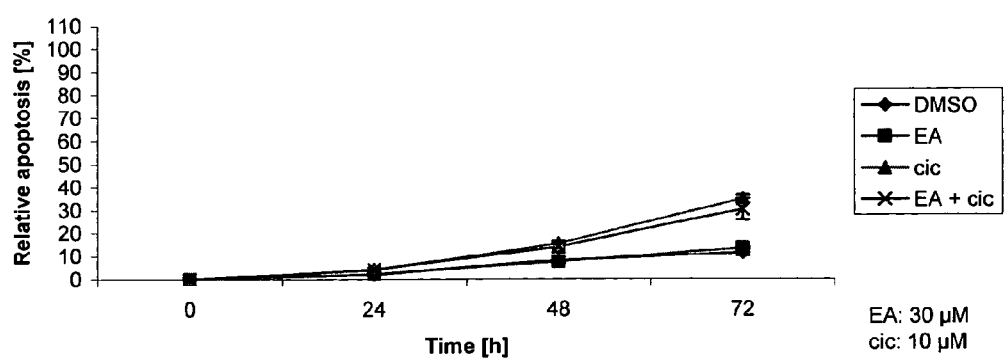
FIG. 12 shows the relative apoptosis of the cell line OPM-2 exposed to EA (30 μM), cic (10 μM) and the combination of EA (30 μM) together with cic (10 μM). DMSO, the solvent of EA and cic, was given to the cell line OPM-2 in a ratio of 1:100, as control. The values are related to the culture-control and expressed as mean±standard error of the mean (SEM) taken from 5 separate measurements.
Figure 12:
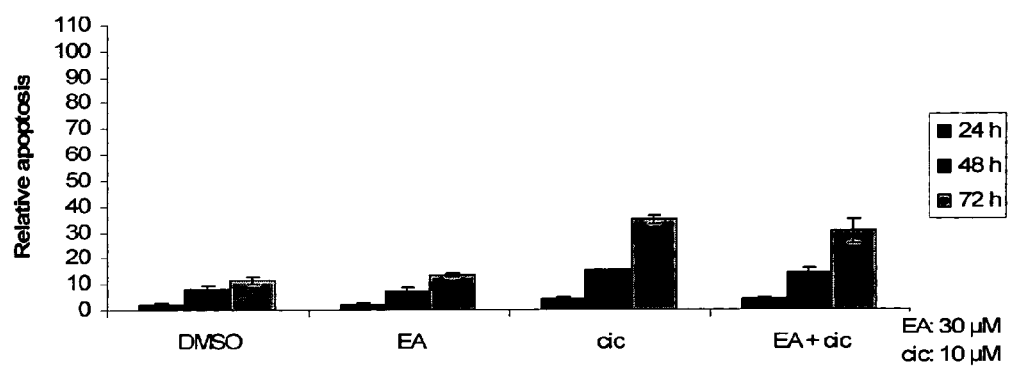

After 72 h, the relative apoptosis for OPM-2 had its maximum at 34.8% for cic (10 μM) followed by 30.2% for the combination of EA (30 μM) together with cic (10 μM) (FIG. 12, Tab. 8). For EA (30 μM), the relative apoptosis was a little bit higher with 13.4 compared to the DMSO-control reaching 11.5%. The apoptosis for OPM-2 induced by DMSO was higher than for the lymphoma cell lines LAM-53, DHL-4 and Raji.

FIG. 12 shows the relative apoptosis of the cell line OPM-2 exposed to EA (30 μM), cic (10 μM) and the combination of EA (30 μM) together with cic (10 μM). DMSO, the solvent of EA and cic, was given to the cell line OPM-2 in a ratio of 1:100, as control. The values are related to the culture-control and expressed as mean±standard error of the mean (SEM) taken from 5 separate measurements. In FIG. 12 (A) samples were measured after 24, 48 and 72 h. After 0 h, the time of execution, the relative apoptosis was defined as 0% for all samples. In FIG. 12 (B) the relative apoptosis values for the samples measured after 24, 48 and 72 h.

Example 6

The Relative Viability of the Cell Line Raji Exposed to EA (30 μM), cic (10 μM) and the Combination of EA (30 μM) Together with cic (10 μM)

Figure 13:
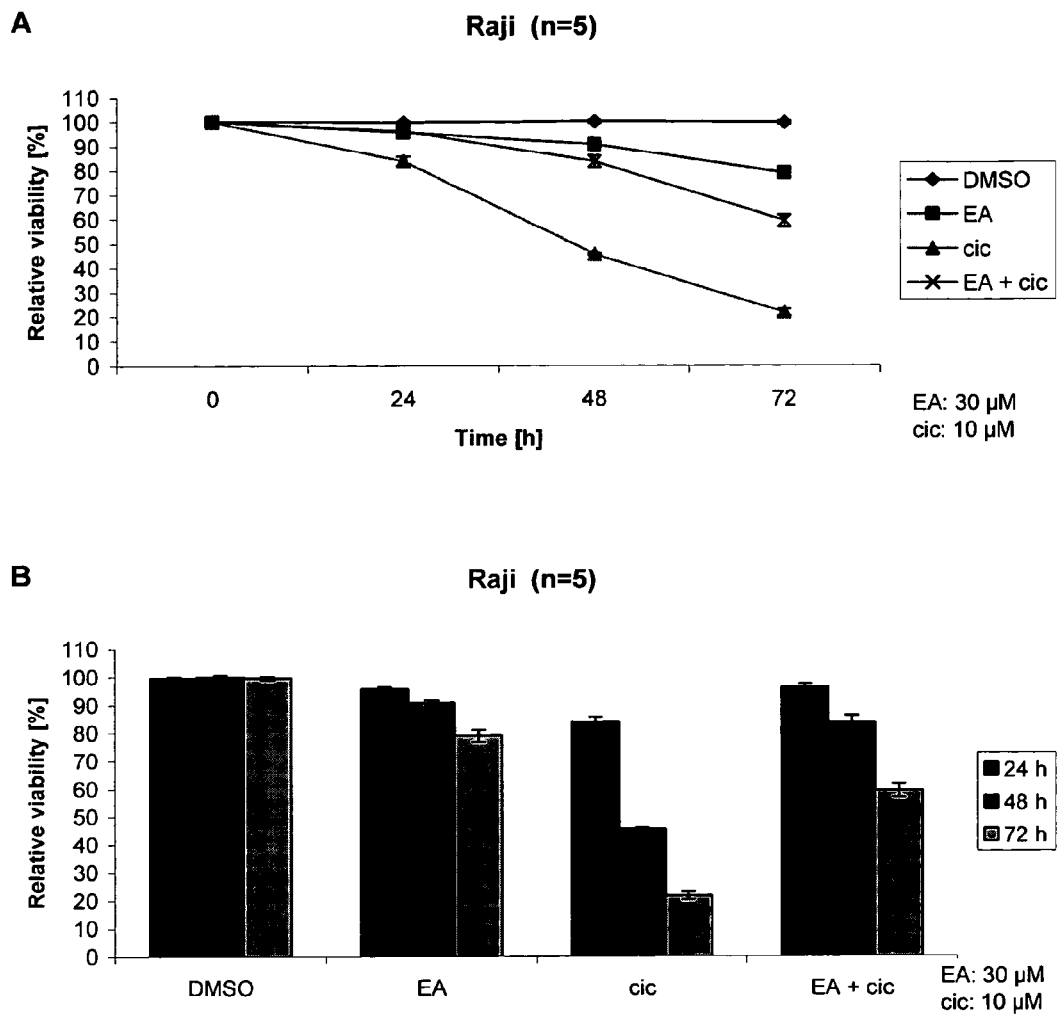
FIG. 13 shows the relative viability of the cell line Raji exposed to EA (30 μM), cic (10 μM) and the combination of EA (30 μM) together with cic (10 μM). DMSO, the solvent of EA and cic, was given to the cell line Raji in a ratio of 1:100, as control. The values are related to the culture-control and expressed as mean±standard error of the mean (SEM) taken from 5 separate measurements.

The strongest decrease in relative viability for Raji was observed after 72 h for cic (10 μM) with 21.7% (FIG. 13, Tab. 9). The values decreased in a logarithmically manner for EA (30 μM) down to 78.9% and for the combination of EA (30 μM) together with cic (10 μM) down to 59.3% until 72 h. For the DMSO-control no significant deviation was detected over the 72 h time period. Again, the highest difference in the relative viability compared to the PBMCs reached the concentration of cic (10 μM) after 72 h with 21.7% for Raji and 94.4% for the PBMCs.

TABLE 8

The relative apoptosis for the cell line OPM-2 given in %.

Culture = 0%

| Time [h]: | DMSO: | ±SEM: | 30 μM EA: | ±SEM: | P-value: | 10 μM cic: | ±SEM: | P-value: |
|---|---|---|---|---|---|---|---|---|
| 0 | 0.0 | 0.0 | 0.0 | 0.0 | — | 0.0 | 0.0 | — |
| 24 | 2.0 | 0.7 | 2.3 | 0.7 | 0.789 | 4.0 | 0.6 | 0.057 |
| 48 | 8.1 | 1.4 | 7.5 | 1.0 | 0.736 | 15.3 | 0.3 | 0.001 |
| 72 | 11.5 | 1.5 | 13.4 | 0.5 | 0.243 | 34.8 | 1.7 | 0.000 |

| | Culture = 0% | | 30 μM EA + | | |
|---|---|---|---|---|---|
| Time [h]: | DMSO: | ±SEM: | 10 μM cic: | ±SEM: | P-value: |
| 0 | 0.0 | 0.0 | 0.0 | 0.0 | — |
| 24 | 2.0 | 0.7 | 4.0 | 0.9 | 0.112 |
| 48 | 8.1 | 1.4 | 14.0 | 2.4 | 0.071 |
| 72 | 11.5 | 1.5 | 30.2 | 4.6 | 0.005 |

FIG. 13 shows the relative viability of the cell line Raji exposed to EA (30 μM), cic (10 μM) and the combination of EA (30 μM) together with cic (10 μM). DMSO, the solvent of EA and cic, was given to the cell line Raji in a ratio of 1:100, as control. The values are related to the culture-control and expressed as mean±standard error of the mean (SEM) taken from 5 separate measurements. In FIG. 13 (A) samples were measured after 24, 48 and 72 h. After 0 h, the time of execution, the relative viability was defined as 100% for all samples. In FIG. 13 (B) the relative viability values for the samples measured after 24, 48 and 72 h.

TABLE 9

The relative viability for the cell line Raji given in %.

| Culture = 100% | | | | | | | | |
| --- | --- | --- | --- | --- | --- | --- | --- | --- |
| Time [h]: | DMSO: | ±SEM: | 30 μM EA: | ±SEM: | P-value: | 10 μM cic: | ±SEM: | P-value: |
| 0 | 100.0 | 0.0 | 100.0 | 0.0 | — | 100.0 | 0.0 | — |
| 24 | 99.6 | 0.3 | 95.7 | 0.6 | 0.001 | 83.8 | 1.8 | 0.000 |
| 48 | 100.1 | 0.7 | 90.7 | 1.0 | 0.000 | 45.6 | 0.4 | 0.000 |
| 72 | 99.6 | 0.7 | 78.9 | 2.1 | 0.000 | 21.7 | 1.4 | 0.000 |

| Culture = 100% | | | 30 μM EA + | | |
| --- | --- | --- | --- | --- | --- |
| Time [h]: | DMSO: | ±SEM: | 10 μM cic: | ±SEM: | P-value: |
| 0 | 100.0 | 0.0 | 100.0 | 0.0 | — |
| 24 | 99.6 | 0.3 | 96.1 | 1.3 | 0.028 |
| 48 | 100.1 | 0.7 | 83.7 | 2.4 | 0.000 |
| 72 | 99.6 | 0.7 | 59.3 | 2.3 | 0.000 |

Figure 14:
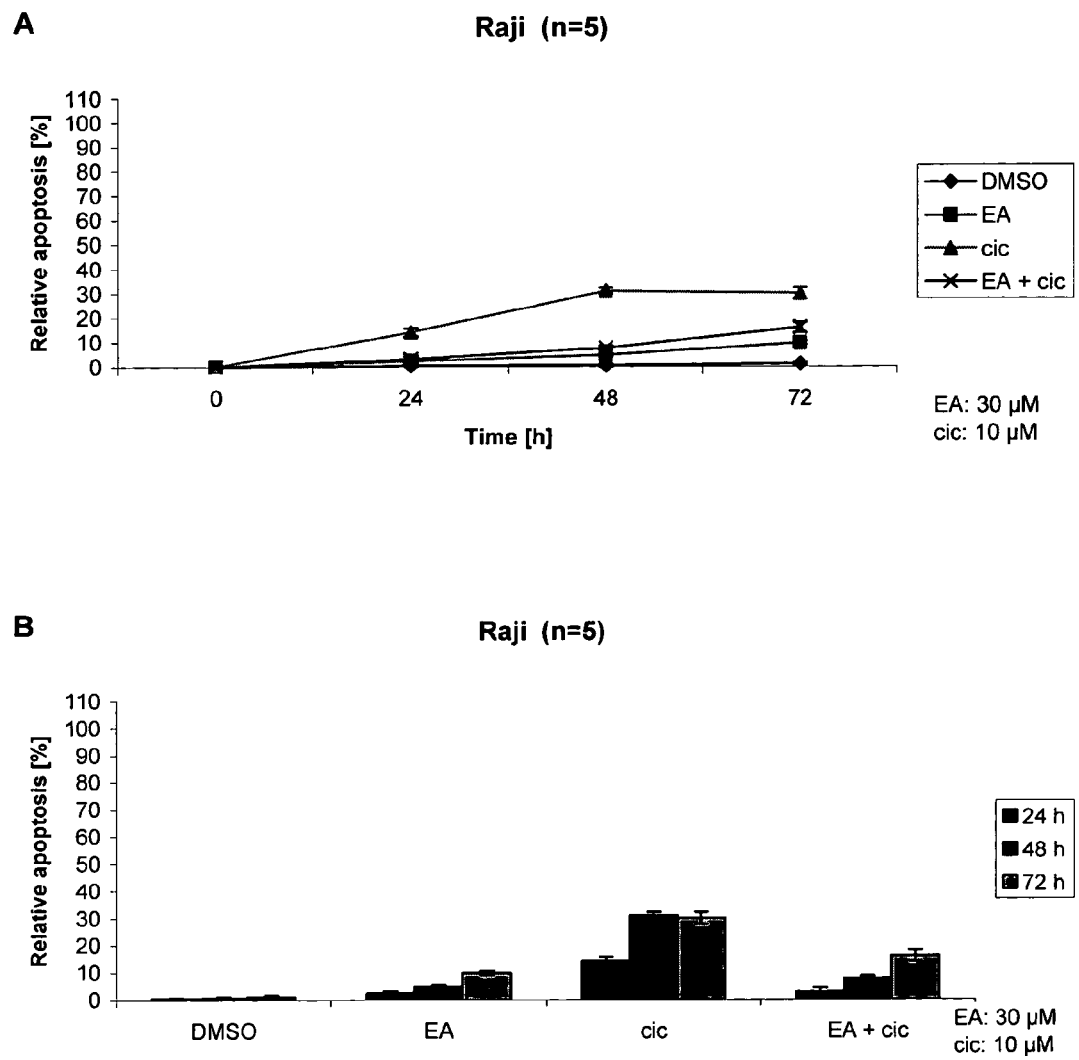
FIG. 14 shows the relative apoptosis of the cell line Raji exposed to EA (30 μM), cic (10 μM) and the combination of EA (30 μM) together with cic (10 μM). DMSO, the solvent of EA and cic, was given to the cell line Raji in a ratio of 1:100, as control. The values are related to the culture-control and expressed as mean±standard error of the mean (SEM) taken from 5 separate measurements.

The maximum value for relative apoptosis could be observed already after 48 h for cic (10 μM) with 31.0% then decreasing to 30.0% after 72 h (FIG. 14, Tab. 10). This was nearly two times higher than for the combination of EA (30 μM) together with cic (10 μM) after 72 h with 16.0%. The relative apoptosis for EA (30 μM) increased constantly over the 72 h time period with 2.4% after 24 h to 4.8% after 48 h and reaching finally 9.8% after 72 h.

FIG. 14 shows the relative apoptosis of the cell line Raji exposed to EA (30 μM), cic (10 μM) and the combination of EA (30 μM) together with cic (10 μM). DMSO, the solvent of EA and cic, was given to the cell line Raji in a ratio of 1:100, as control. The values are related to the culture-control and expressed as mean±standard error of the mean (SEM) taken from 5 separate measurements. In FIG. 14 (A) samples were measured after 24, 48 and 72 h. After 0 h, the time of execution, the relative apoptosis was defined as 0% for all samples. In FIG. 14 (B) the relative apoptosis values for the samples measured after 24, 48 and 72 h.

TABLE 10

The relative apoptosis for the cell line Raji given in %.

| Culture = 0% | | | | | | | | |
| --- | --- | --- | --- | --- | --- | --- | --- | --- |
| Time [h]: | DMSO: | ±SEM: | 30 μM EA: | ±SEM: | P-value: | 10 μM cic: | ±SEM: | P-value: |
| 0 | 0.0 | 0.0 | 0.0 | 0.0 | — | 0.0 | 0.0 | — |
| 24 | 0.5 | 0.3 | 2.4 | 0.8 | 0.063 | 14.1 | 1.6 | 0.000 |
| 48 | 0.6 | 0.6 | 4.8 | 0.5 | 0.001 | 31.0 | 1.3 | 0.000 |
| 72 | 1.2 | 0.6 | 9.8 | 0.7 | 0.000 | 30.0 | 2.3 | 0.000 |

| Culture = 0% | | | 30 μM EA + | | |
| --- | --- | --- | --- | --- | --- |
| Time [h]: | DMSO: | ±SEM: | 10 μM cic: | ±SEM: | P-value: |
| 0 | 0.0 | 0.0 | 0.0 | 0.0 | — |
| 24 | 0.5 | 0.3 | 3.0 | 1.3 | 0.108 |
| 48 | 0.6 | 0.6 | 7.7 | 1.0 | 0.000 |
| 72 | 1.2 | 0.6 | 16.0 | 2.0 | 0.000 |

After 72 h, the relative viability for the lymphoma cell lines with EA (30 μM) had the order DHL-4>LAM-53>Raji with values of 97.6%, 91.0% and 78.9%. For cic (10 μM), the order was the same with DHL-4>LAM-53>Raji indicating relative viability values of 55.9%, 32.4% and 21.7%. The combination of EA (30 μM) together with dc (10 μM) showed an order of Raji>DHL-4>LAM-53 giving values of 59.3%, 50.8% and 46.0%, respectively.

The invention claimed is:

1. A composition comprising one or more compounds in a dosage unit form, wherein the one or more compounds are selected from the group consisting of a) compound (I) which is ethacrynic acid

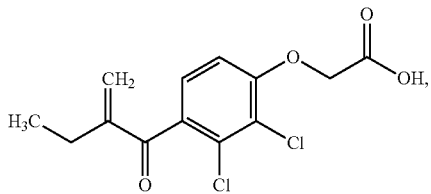 [SMILES: C=C(CC)C(=O)c1ccc(OCC(=O)O)c(Cl)c1Cl]

in an amount ranging from approximately 1 to 1000 mg, b) compound (II), which is ciclopirox

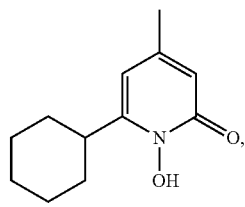

in an amount ranging from approximately 1 to 1000 mg, and c) mixtures of compound (I) and compound (II) for the treatment of cancer selected from the group consisting myeloma, lymphoma and leukemia.

2. The composition according to claim 1, wherein the the composition is adapted for oral, parenteral, rectal, nasal, vaginal, or topical administration.

* * * * *